US012788529B2

(12) United States Patent
Brandao et al.

(10) Patent No.: US 12,788,529 B2
(45) Date of Patent: Nov. 10, 2026

(54) SURGICAL SYSTEM WITH MULTI-MODALITY IMAGE DISPLAY

(71) Applicant: Intuitive Surgical Operations, Inc., Sunnyvale, CA (US)

(72) Inventors: Karen C. Brandao, San Jose, CA (US); Mahdi Azizian, Santa Clara, CA (US); Simon P. DiMaio, San Carlos, CA (US); Brian D. Hoffman, Mountain View, CA (US); Jonathan M. Sorger, Belmont, CA (US)

(73) Assignee: Intuitive Surgical Operations, Inc., Sunnyvale, CA (US)

(*) Notice: Subject to any disclaimer, the term of this patent is extended or adjusted under 35 U.S.C. 154(b) by 1131 days.

(21) Appl. No.: 16/349,216

(22) PCT Filed: Nov. 10, 2017

(86) PCT No.: PCT/US2017/061151
§ 371 (c)(1),
(2) Date: May 10, 2019

(87) PCT Pub. No.: WO2018/089827
PCT Pub. Date: May 17, 2018

(65) Prior Publication Data

US 2020/0188057 A1 Jun. 18, 2020

Related U.S. Application Data

(60) Provisional application No. 62/421,095, filed on Nov. 11, 2016.

(51) Int. Cl.
*A61B 90/00* (2016.01)
*A61B 34/10* (2016.01)
(Continued)

(52) U.S. Cl.
CPC ............ *A61B 90/361* (2016.02); *A61B 34/10* (2016.02); *A61B 34/20* (2016.02); *A61B 34/37* (2016.02);
(Continued)

(58) Field of Classification Search
CPC ....... A61B 90/361; A61B 34/10; A61B 34/20; A61B 34/37; A61B 2034/101;
(Continued)

(56) References Cited

U.S. PATENT DOCUMENTS 7,951,070 B2 5/2011 Ozaki et al.
8,682,413 B2 3/2014 Lloyd
(Continued)

FOREIGN PATENT DOCUMENTS

CN 102470014 A 5/2012
CN 103948432 A 7/2014
(Continued)

OTHER PUBLICATIONS

Extended European Search Report for Application No. EP17869267.9 mailed on Nov. 11, 2020, 7 pages.
(Continued)

*Primary Examiner* — Sanjay Cattungal
(74) *Attorney, Agent, or Firm* — Foley & Lardner LLP

(57) ABSTRACT

A method is provided to produce a multi-modality image of a surgical scene comprising: capture light reflected from the surgical scene; producing first image information corresponding to a first modality image; producing second image information corresponding to a second modality image; selecting a portion of the second image modality based at least in part upon anatomical structure information included within the selected portion; and producing simultaneously
(Continued)

within a display at least a portion of the first modality image of the surgical scene and the selected portion of the second modality image.

20 Claims, 21 Drawing Sheets

(51) Int. Cl.
*A61B 34/20* (2016.01)
*A61B 34/37* (2016.01)

(52) U.S. Cl.
CPC ... *A61B 2034/101* (2016.02); *A61B 2090/364* (2016.02); *A61B 2090/371* (2016.02)

(58) Field of Classification Search
CPC ........ A61B 2090/364; A61B 2090/371; A61B 90/00; A61B 2017/00216
See application file for complete search history.

(56) References Cited

U.S. PATENT DOCUMENTS

| | | | | |
|---|---|---|---|---|
| 9,436,993 | B1 * | 9/2016 | Stolka | G06T 5/001 |
| 9,770,172 | B2 * | 9/2017 | Sturm | A61B 8/4416 |
| 2009/0192519 | A1 | 7/2009 | Omori | |
| 2011/0157154 | A1 * | 6/2011 | Bernard | A61B 6/5229 345/419 |
| 2012/0089014 | A1 | 4/2012 | Sabczynski et al. | |
| 2012/0106702 | A1 * | 5/2012 | Feke | A61B 6/5235 378/63 |
| 2012/0224787 | A1 * | 9/2012 | Imai | H04N 23/64 382/274 |
| 2014/0005531 | A1 * | 1/2014 | Taylor | A61B 5/06 600/424 |
| 2014/0277542 | A1 * | 9/2014 | Stein | A61F 2/4657 623/20.32 |
| 2015/0018622 | A1 | 1/2015 | Tesar et al. | |
| 2016/0007909 | A1 * | 1/2016 | Singh | A61F 2/4657 606/102 |
| 2016/0360117 | A1 * | 12/2016 | Elefteriu | G16H 30/40 |
| 2017/0100037 | A1 * | 4/2017 | Harmelin | A61B 5/0042 |
| 2018/0249977 | A1 * | 9/2018 | Melman | A61B 6/5205 |
| 2018/0270474 | A1 * | 9/2018 | Liu | H04N 13/254 |
| 2019/0290374 | A1 * | 9/2019 | Ramadorai | A61B 34/30 |
| 2022/0207274 | A1 * | 6/2022 | Folkens | G06V 10/25 |

FOREIGN PATENT DOCUMENTS

| | | | |
|---|---|---|---|
| CN | 105193503 | A | 12/2015 |
| CN | 105395252 | A | 3/2016 |
| EP | 2341482 | A2 | 7/2011 |
| JP | H10137190 | A | 5/1998 |
| JP | 2005251193 | A | 9/2005 |
| JP | 2007135828 | A | 6/2007 |
| JP | 2007259481 | A | 10/2007 |
| JP | 2009226072 | A | 10/2009 |
| JP | 2010256580 | A | 11/2010 |
| JP | 2014053737 | A | 3/2014 |
| JP | 2016077769 | A | 5/2016 |
| KR | 20130108320 | A | 10/2013 |
| KR | 101630539 | B1 | 6/2016 |
| WO | WO-2006095027 | A1 | 9/2006 |
| WO | WO-2012033552 | A1 | 3/2012 |
| WO | WO-2015126466 | A1 | 8/2015 |
| WO | WO-2015143067 | A1 | 9/2015 |

OTHER PUBLICATIONS

Hinsche A.F., et al., "Image-Guided Surgery" Current Orthopaedics, Aug. 2001, vol. 15(1), pp. 296-303.
International Preliminary Report on Patentability for Application No. PCT/US2017/061151, mailed on May 23, 2019, 14 pages.
International Search Report and Written Opinion for Application No. PCT/US2017/061151, mailed on Feb. 28, 2018, 18 pages.
Kenny K., et al., "Raman Spectroscopy for Medical Diagnostics—from In-Vitro Biofluid Assays to In-Vivo Cancer Detection," Advanced Drug Delivery Reviews, Jul. 2015, vol. 89, pp. 121-134.
Kobayashi H., et al., "New Strategies for Fluorescent Probe Design in Medical Diagnostic Imaging," Chemical Reviews, May 2010, vol. 110(5), pp. 2620-2640.
Kuznetsov K., et al., "Narrow-Band Imaging: Potential and Limitations," Endoscopy, Jan. 2006. vol. 38(1), pp. 76-81.
Lu G., etal., "Medical Hyperspectral Imaging: a Review," Journal of Biomedical Optics, Jan. 2014, vol. 19(1), pp. 10901-1 to 10901-23.
Vertut, Jean and Phillipe Coiffet. Robot Technology: Teleoperation and Robotics Evolution and Development, English translation, Prentice-Hall, Inc., Inglewood Cliffs, NJ, USA 1986, vol. 3A, 332 pages.
Extended European Search Report for Application No. EP24174918.3, mailed on May 29, 2024, 08 pages.
Extended European Search Report for Application No. EP26155140.2, mailed on Jun. 3, 2026, 8 pages.

* cited by examiner

2402
| Modality | Selected? |
|---|---|
| NBI | X |
| Raman Spectroscopy | |
| Fluorescence | X |
| Hyperspectral Imaging | |
FIG. 24
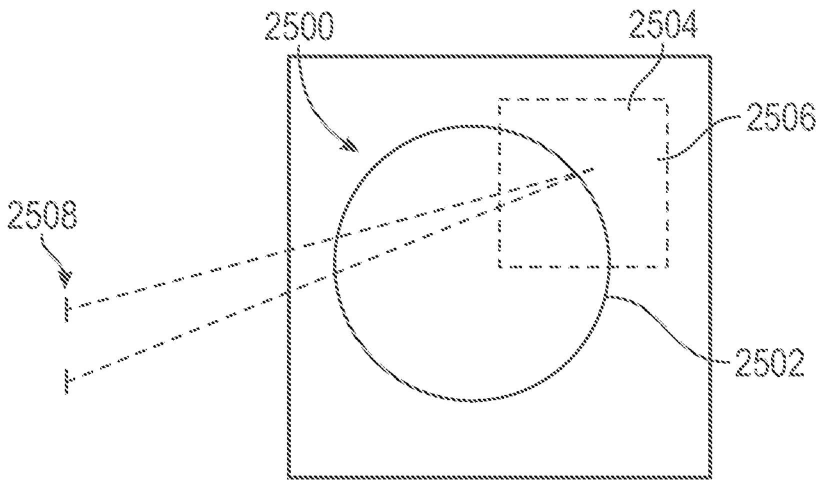
FIG. 25A
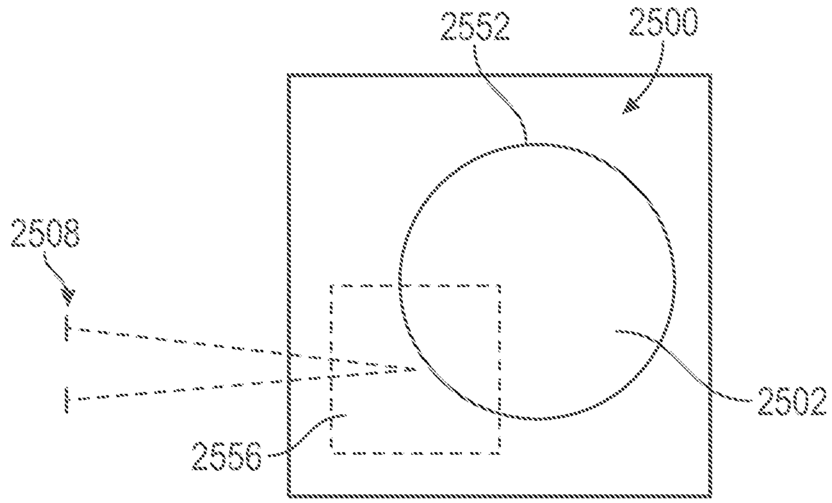
FIG. 25B

2702

2704

| Modality | Full-Screen | Insert |
|---|---|---|
| Clear | X2 | |
| NBI | X1 | |
| Raman Spectroscopy | | X |
| Fluorescence | | X |
| Hyperspectral Imaging | | X |

2706

| Presentation Style | Selection |
|---|---|
| Stitch | |
| PiP | X |
| Annotate | |

2902

| Surgical Stage Signature | Modality |
|---|---|
| SigSS1 | NBI |
| SigSS2 | NBI |
| SigSS3 | Fluorescence |
| SigSS4 | Raman |
| SigSS5 | Fluorescence |
| ... | ... |
| SigSSn-2 | HSI |
| SigSSn-1 | NBI |
| SigSSn | Fluorescence |

3102

| Image Signature | Annotation |
|---|---|
| SigIM.1 | Annot.1 |
| SigIM.2 | Annot.2 |
| SigIM.3 | Annot.3 |
| ... | ... |
| SigIM.n-2 | Annot.n-2 |
| SigIM.n-1 | Annot.n-1 |
| SigIM.n | Annot.n |

SURGICAL SYSTEM WITH MULTI-MODALITY IMAGE DISPLAY

CLAIM OF PRIORITY

This application is a U.S. National Stage Filing under 35 U.S.C. 371 from International Application No. PCT/US2017/061151, filed on Nov. 10, 2017, and published as WO 2018/089827 A1 on May 17, 2018, which claims the benefit of priority to U.S. Patent Application No. 62/421,095, filed on Nov. 11, 2016, each of which is hereby incorporated by reference herein in its entirety.

BACKGROUND

Image guided surgical techniques provide surgeons with the ability to visualize internal structures of anatomical objects within a surgical scene. Improved visualization abilities allow a surgeon to better perceive the actual position of surgical instruments and their physical relationship to critical or hidden anatomical structures within anatomical objects, which can result in safer and more effective minimally invasive surgical procedures.

SUMMARY

The following summary introduces certain aspects of the inventive subject matter in order to provide a basic understanding. This summary is not an extensive overview of the inventive subject matter, and it is not intended to identify key or critical elements or to delineate the scope of the inventive subject matter. Although this summary contains information that is relevant to various aspects and embodiments of the inventive subject matter, its sole purpose is to present some aspects and embodiments in a general form as a prelude to the more detailed description below.

In one aspect, a method is provided to produce a multi-modality image of a surgical scene. A camera captures light reflected from the surgical scene. First image information is produced that corresponds to a first modality image of the surgical scene. Second modality image information is produced that corresponds to the surgical scene. A portion of the second image modality is selected based at least in part upon anatomic structural information that it contains. A computer is configured to use the first image information and the second image information to produce simultaneously within a display at least a portion of the first modality image of the surgical scene and the selected portion of the second modality image of the surgical scene.

In another aspect, a method is provided to produce a multi-modality image of a surgical scene. A camera captures light reflected from the surgical scene. First image information is produced corresponding to a first modality image of the surgical scene. Second image information is produced corresponding to a second modality image of the surgical scene. User eye focus location is tracked within a display. A portion of the second modality image is selected based at least in part upon tracked user eye focus. A computer is configured to use the first image information and the second image information to produce simultaneously within the display at least a portion of the first modality image of the surgical scene and the selected portion of the second modality image of the surgical scene.

In yet another aspect, a method is provided to produce a multi-modality image of a surgical scene. A camera captures light reflected from the surgical scene. First image information is produced corresponding to a first modality image of the surgical scene. Second image information is produced corresponding to a second modality image of the surgical scene. Surgical stage is tracked in the course of a surgical procedure. A modality image format is selected based at least in part upon the tracked surgical stage. A computer is configured to use the first image information and the second image information to produce within a display in the selected format, at least a portion of the first modality image and at least a portion of the second modality image.

BRIEF DESCRIPTION OF THE DRAWINGS

FIG. 24 is an illustrative drawing representing an example modality selection user interface UI displayed within a viewer of the surgical system in accordance with some embodiments.

FIGS. 25A-C are illustrative drawings presenting two dimensional eye tracking (FIGS. 25A-2513) and depth eye tracking (FIG. 25C) in accordance with some embodiments.

DETAILED DESCRIPTION

Figure 1:
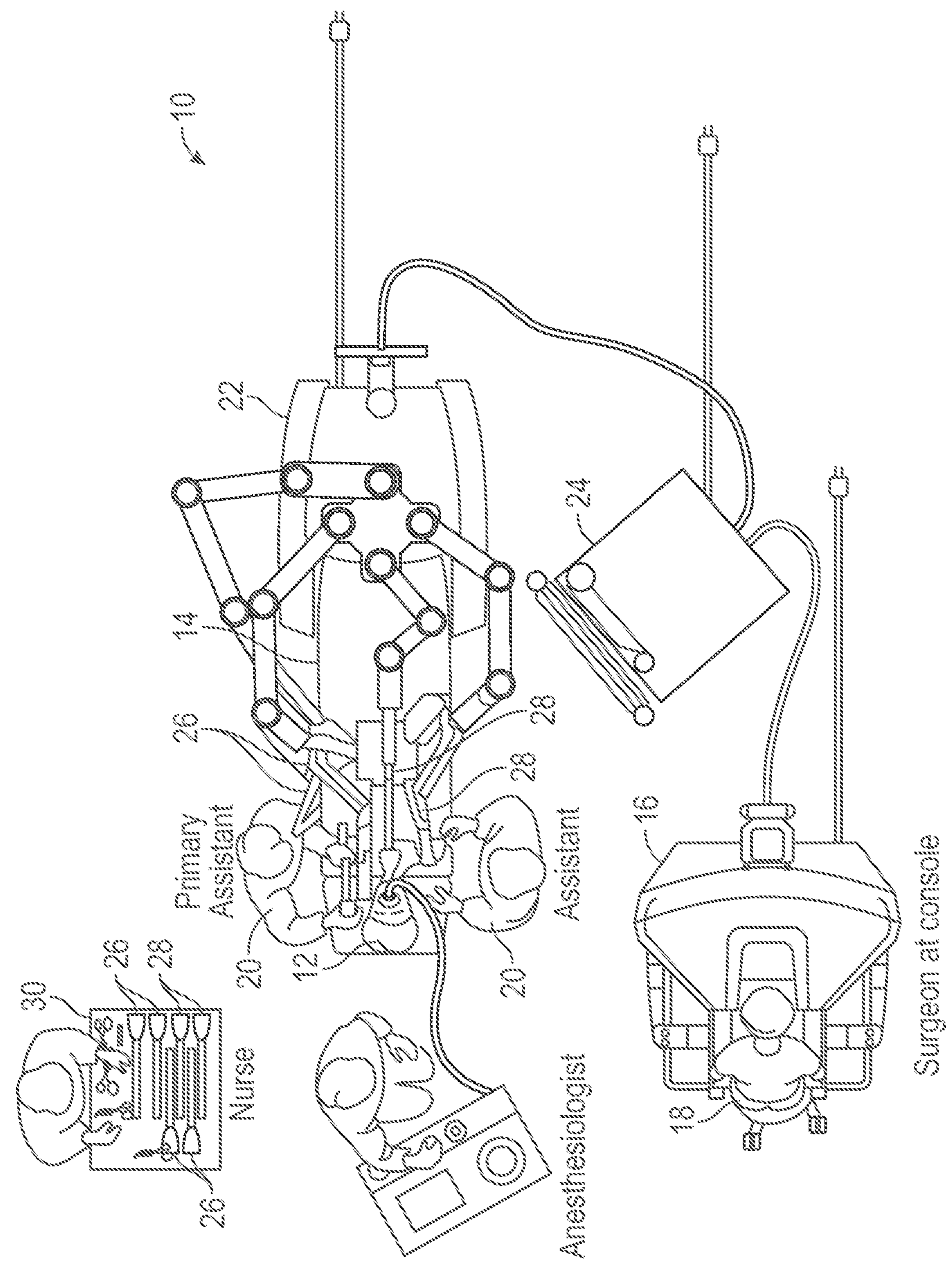
FIG. 1 is a plan view of a minimally invasive teleoperated surgical system.

This description and the accompanying drawings that illustrate inventive aspects, embodiments, implementations, or applications should not be taken as limiting—the claims define the protected invention. Various mechanical, compositional, structural, electrical, and operational changes may be made without departing from the scope of this description and the claims. In some instances, well-known circuits, structures, or techniques have not been shown or described in detail in order not to obscure the invention. Like numbers in two or more figures represent the same or similar elements.

The following description is presented to enable any person skilled in the art to create and use a multi-modality image in a surgical system. Various modifications to the embodiments will be readily apparent to those skilled in the art, and the generic principles defined herein may be applied to other embodiments and applications without departing from the scope of the inventive subject matter. Moreover, in the following description, numerous details are set forth for the purpose of explanation. However, one of ordinary skill in the art will realize that the inventive subject matter might be practiced without the use of these specific details. In other instances, well-known machine components, processes and data structures are shown in block diagram form in order not to obscure the disclosure with unnecessary detail. Identical reference numerals may be used to represent different views of the same item in different drawings. Flow diagrams in drawings referenced below are used to represent processes. A computer system may be configured to perform some of these processes. Blocks within flow diagrams representing computer implemented processes represent the configuration of a computer system according to computer program code to perform the acts described with reference to these modules. Thus, the inventive subject matter is not intended to be limited to the embodiments shown, but is to be accorded the widest scope consistent with the principles and features disclosed herein.

Minimally Invasive Teleoperated Surgical System

Teleoperation refers to operation of a machine at a distance. In a minimally invasive teleoperation medical system, a surgeon may use an endoscope that includes a camera to view a surgical site within a patient's body. In some embodiments, stereoscopic images can be captured, which allow the perception of depth during a surgical procedure.

FIG. 1 is an illustrative plan view of a minimally invasive teleoperated surgical system 10, typically used for performing a minimally invasive diagnostic or surgical procedure on a patient 12 who is lying on an operating table 14. The system includes a surgeon's console 16 for use by a surgeon 18 during the procedure. One or more assistants 20 may also participate in the procedure. The minimally invasive teleoperated surgical system 10 further includes a patient-side cart(s) 22 and an electronics cart 24. The patient-side cart 22 can manipulate at least one surgical instrument 26 through a minimally invasive incision in the body of the patient 12 while the surgeon 18 views the surgical site through the surgeon's console 16. An image of the surgical site can be obtained by an endoscope 28, such as a stereoscopic endoscope, which can be manipulated by the patient-side cart 22 to orient the endoscope 28. Computer processors located on the electronics cart 24 can be used to process the images of the surgical site for subsequent display to the surgeon 18 through the surgeon's console 16. Note that while discrete system components (i.e., patient side cart 22, electronics cart 24, and surgeon's console 16) are depicted and described for exemplary purposes, in various embodiments the elements included therein can be combined and/or separated. For example, in some embodiments, the computer processors of electronics cart 24 can be incorporated into surgeon's console 16 and/or patient side cart 22. The number of surgical instruments 26 used at one time will generally depend on the diagnostic or surgical procedure and the space constraints within the operative site among other factors. If it is necessary to change one or more of the surgical instruments 26 being used during a procedure, an assistant 20 can remove the surgical instrument 26 from the patient-side cart 22, and replace it with another surgical instrument 26 from a tray 30 in the operating room.

Figure 2:
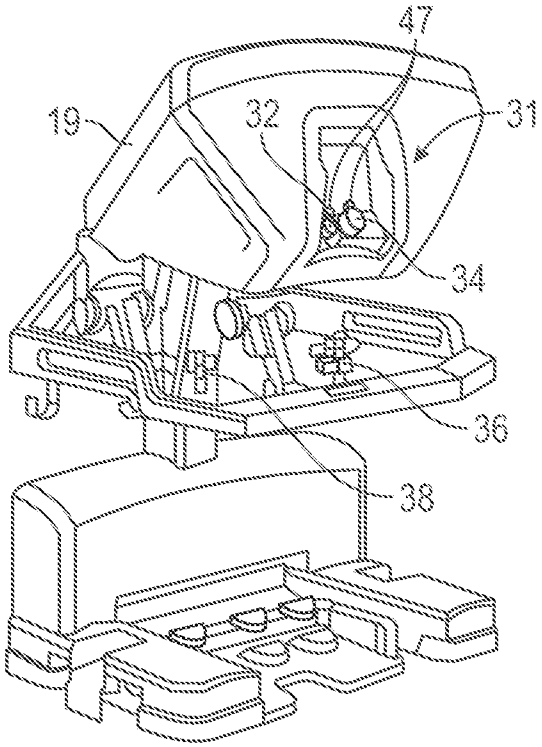
FIG. 2 is a perspective view of a surgeon's console.

FIG. 2 is a perspective view of the surgeon's console 16. The surgeon's console 16 includes a viewer display 31 that includes a left eye display 32 and a right eye display 34 for presenting the surgeon 18 with a coordinated stereoscopic view of the surgical site that enables depth perception. The console 16 further includes one or more control inputs 36. One or more surgical instruments installed for use on the patient-side cart 22 (shown in FIG. 1) move in response to surgeon 18's manipulation of the one or more control inputs 36. The control inputs 36 can provide the same mechanical degrees of freedom as their associated surgical instruments 26 (shown in FIG. 1) to provide the surgeon 18 with telepresence, or the perception that the control inputs 36 are integral with the instruments 26 so that the surgeon has a strong sense of directly controlling the instruments 26. To this end, position, force, and tactile feedback sensors (not shown) may be employed to transmit position, force, and tactile sensations from the surgical instruments 26 back to the surgeon's hands through the control inputs 36, subject to communication delay constraints. Note that while a physical console 16 with a fixed viewer 31 and mechanically coupled control inputs 36 is depicted and described for exemplary purposes, in various other embodiments, "ungrounded" control inputs and/or display structures can be used. For example, in some embodiments, viewer 31 can be a head-mounted display and/or control inputs 36 can be mechanically independent of any base structure (e.g., wired, wireless, or gesture-based, such as Kinect from Microsoft).

The surgeon's console 16 is usually located in the same room as the patient so that the surgeon can directly monitor the procedure, be physically present if necessary, and speak to a patient-side assistant directly rather than over the telephone or other communication medium. But, the surgeon can be located in a different room, a completely different building, or other remote location from the patient allowing for remote surgical procedures.

Figure 3:
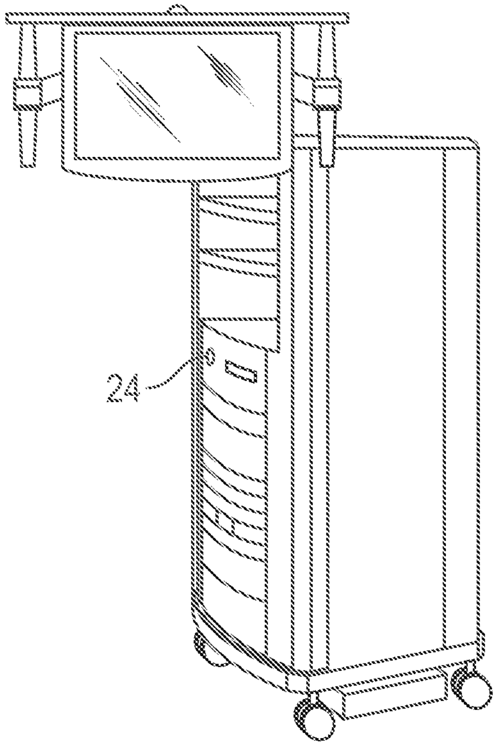
FIG. 3 is a perspective view of an electronics cart.

FIG. 3 is a perspective view of the electronics cart 24. The electronics cart 24 can be coupled with the endoscope 28 and includes a computer processor to process captured images for subsequent display, such as to a surgeon on the surgeon's console, or on another suitable display located locally and/or remotely. For example, if a stereoscopic endoscope is used, a computer processor on electronics cart 24 can process the captured images to present the surgeon with coordinated stereo images of the surgical site. Such coordination can include alignment between the opposing images and can include adjusting the stereo working distance of the stereoscopic endoscope. As another example, image processing can include the use of previously determined camera calibration parameters to compensate for imaging errors of the image capture device, such as optical aberrations. Optionally, equipment in electronics cart may be integrated into the surgeon's console or the patient-side cart, or it may be distributed in various other locations in the operating room.

Figure 4:
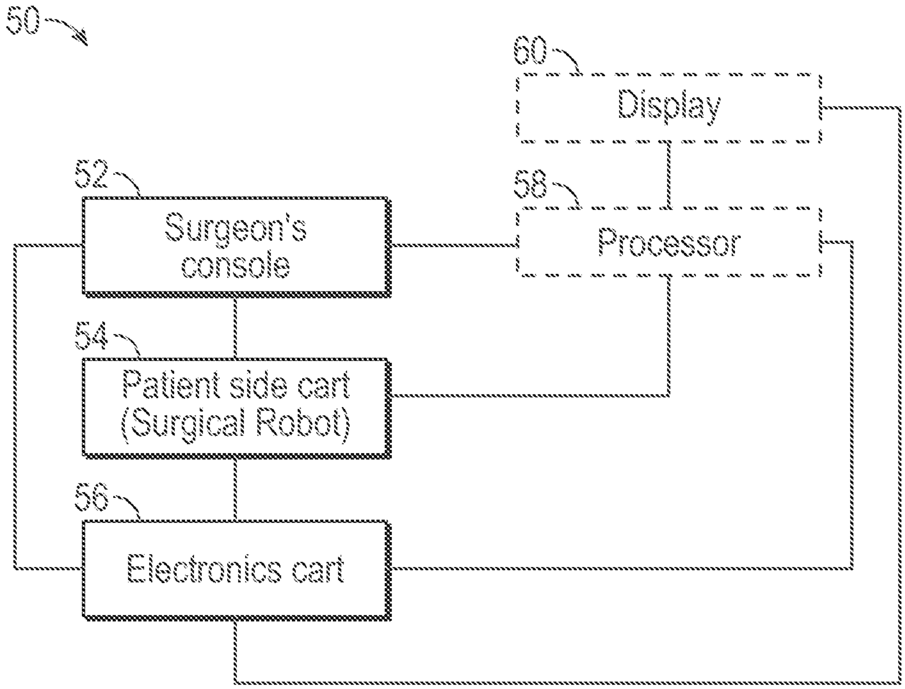
FIG. 4 is a diagrammatic illustration of a teleoperated surgical system.

FIG. 4 diagrammatically illustrates a teleoperated surgical system 50 (such as the minimally invasive teleoperated surgical system 10 of FIG. 1). A surgeon's console 52 (such as surgeon's console 16 in FIG. 1) can be used by a surgeon to control a patient-side cart 54 (such as patient-side cart 22 in FIG. 1) during a minimally invasive procedure. The patient-side cart 54 can use an imaging device, such as a stereoscopic endoscope, to capture images of a surgical site and output the captured images to a computer processor located on an electronics cart 56 (such as the electronics cart 24 in FIG. 1). The computer processor typically includes one or more data processing boards purposed for executing computer readable code stored in a non-volatile memory device of the computer processor. In one aspect, the computer processor can process the captured images in a variety of ways prior to any subsequent display. For example, the computer processor can overlay the captured images with a virtual control interface prior to displaying the combined images to the surgeon via the surgeon's console 52.

Additionally, or in the alternative, the captured images can undergo image processing by a computer processor located outside of electronics cart 56. In one aspect, teleoperated surgical system 50 includes an optional computer processor (CPU) 58 (as indicated by dashed line) similar to the computer processor located on electronics cart 56, and patient-side cart 54 outputs the captured images to computer processor (CPU) 58 for image processing prior to display on the surgeon's console 52. In another aspect, captured images first undergo image processing by the computer processor on electronics cart 56 and then undergo additional image processing by computer processor 58 prior to display on the surgeon's console 52. Teleoperated surgical system 50 can include an optional display 60, as indicated by dashed line. Display 60 is coupled with the computer located on the electronics cart 56 and with computer processor (CPU) 58, and captured images processed by these computer processors can be displayed on display 60 in addition to being displayed on a display of the surgeon's console 52.

Figure 5A:
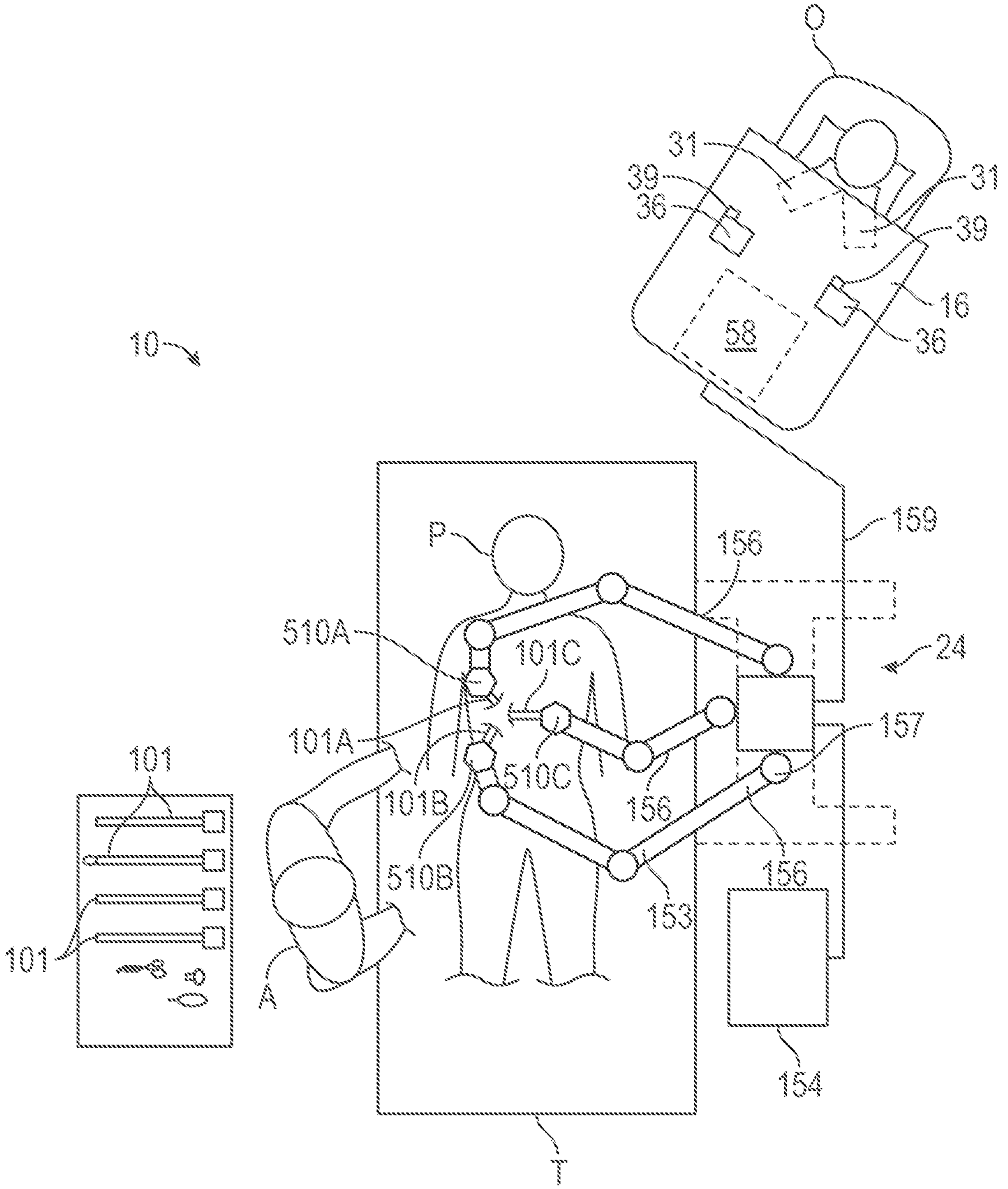
FIG. 5A is an illustrative diagram of the teleoperated surgical system.

FIG. 5A is an illustrative simplified block diagram showing arrangement of components of the teleoperation surgery system 10 to perform surgical procedures using one or more mechanical support arms 510 in accordance with some embodiments. Aspects of system 10 includes robot-assisted and autonomously operating features. These mechanical support arms 510 often support a surgical instrument. For instance, a mechanical surgical arm (e.g., the center mechanical surgical arm 510C) may be used to support an endoscope with a stereo or three-dimensional surgical image capture device 101C. The mechanical surgical arm 510C may include a sterile adapter, or a clamp, clip, screw, slot/groove, or other fastener mechanism to mechanically secure an endoscope that includes the image capture device 101C to the mechanical arm.

A user or operator O (generally a surgeon) performs a surgical procedure on patient P by manipulating control input devices 36, such as hand grips and foot pedals at a master control console 16. The operator can view video frames of images of a surgical site inside a patient's body through a stereo display viewer 31. A computer processor (CPU) 58 of the console 16 directs movement of teleoperationally controlled endoscopic surgical instruments 101A-101C via control lines 159, effecting movement of the instruments using a patient-side system 24 (also referred to as a patient-side cart).

The patient-side system 24 includes one or more mechanical support arms 510. Typically, the patient-side system 24 includes at least three mechanical surgical arms 510A-510C (generally referred to as mechanical surgical support arms 510) supported by corresponding positioning set-up arms 156. The central mechanical surgical arm 510C may support an endoscopic camera 101C suitable for capture of images within a field of view of the camera. The mechanical surgical support arms 510A and 510B to the left and right of center may support instruments 101A and 101B, respectively, which may manipulate tissue.

Figure 5B:
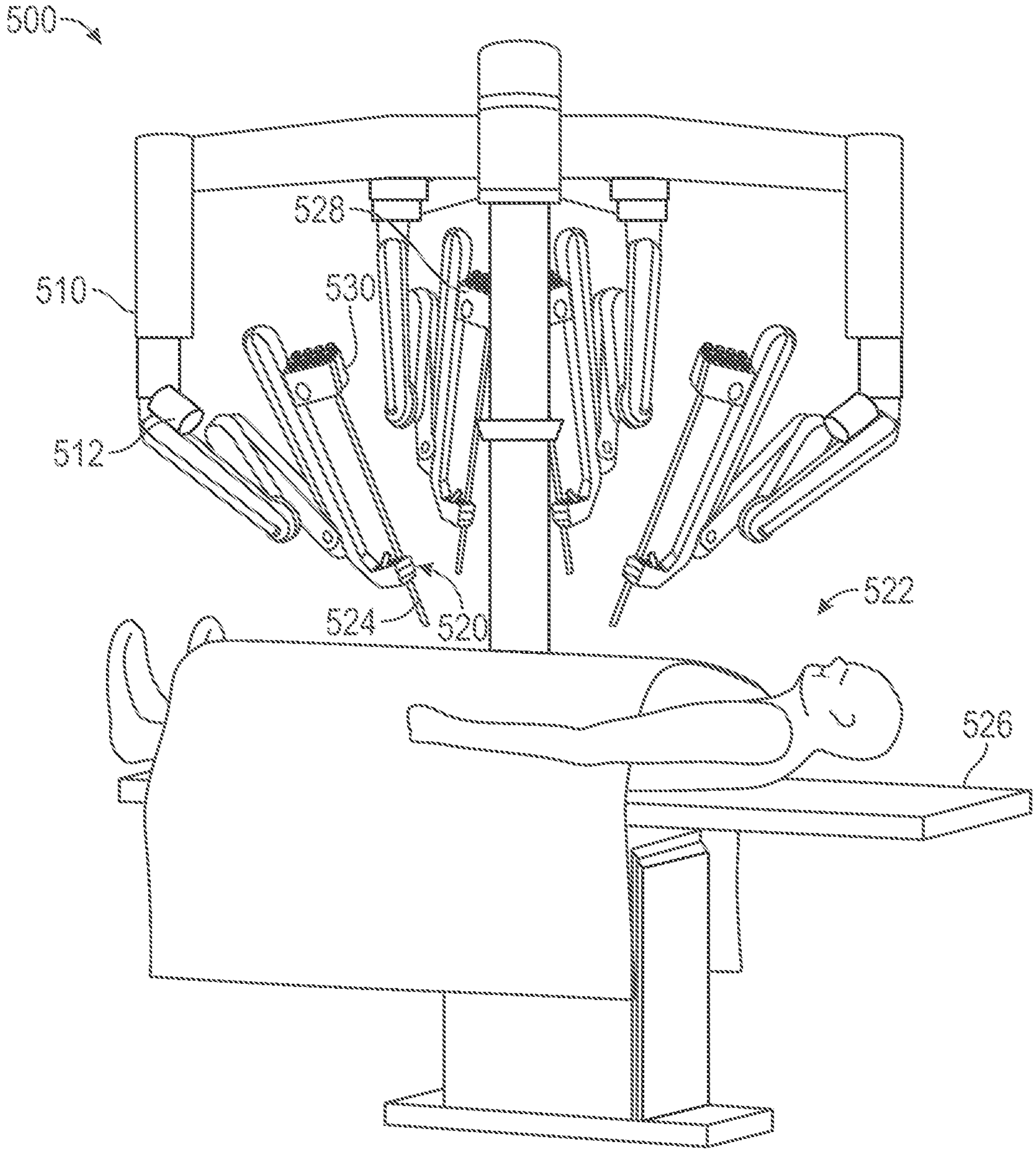
FIG. 5B is a perspective view of a patient-side cart of the surgical system.

FIG. 5B is a perspective view of a patient-side cart 500 of a minimally invasive teleoperated surgical system 10, in accordance with embodiments. The patient-side cart 500 includes one or more support arm assemblies 510. A surgical instrument manipulator 512 is mounted at the end of each support arm assembly 510. Additionally, each support arm assembly 510 can optionally include one or more setup joints (e.g., unpowered and/or lockable) that are used to position the attached surgical instrument manipulator 512 with reference to the patient for surgery. As depicted, the patient-side cart 500 rests on the floor. In other embodiments, operative portions of the patient-side cart can be mounted to a wall, to the ceiling, to the operating table 526 that also supports the patient's body 522, or to other operating room equipment. Further, while the patient-side cart 500 is shown as including four surgical instrument manipulators 512, more or fewer surgical instrument manipulators 512 may be used.

A functional teleoperated surgical system will generally include a vision system portion that enables a user of the teleoperated surgical system to view the surgical site from outside the patient's body 522. The vision system typically includes a camera instrument 528 for capturing video images and one or more video displays for displaying the captured video images. In some surgical system configurations, the camera instrument 528 includes optics that transfer the images from a distal end of the camera instrument 528 to one or more imaging sensors (e.g., CCD or CMOS sensors) that produce digital image information outside of the patients body 522. Alternatively, the imaging sensor(s) can be positioned at the distal end of the camera instrument 528, and digital image information signals produced by the sensor(s) can be transmitted along a lead or wirelessly for processing and display on the one or more video displays. One example of a video display is the stereoscopic display on the surgeon's console in surgical systems commercialized by Intuitive Surgical, Inc., Sunnyvale, California.

Referring to FIGS. 5A-5B, mounted to each surgical instrument manipulator 512 is a surgical instrument 520 that operates at a surgical site within the patient's body 522. Each surgical instrument manipulator 512 can be provided in a variety of forms that allow the associated surgical instrument to move with one or more mechanical degrees of freedom (e.g., all six Cartesian degrees of freedom, five or fewer Cartesian degrees of freedom, etc.). Typically, mechanical or control constraints restrict each manipulator 512 to move its associated surgical instrument around a center of motion on the instrument that stays stationary with reference to the patient, and this center of motion is typically located at the position where the instrument enters the body.

In one aspect, surgical instruments 520 are controlled through computer-assisted teleoperation. A functional minimally invasive teleoperated surgical system includes a control input that receives inputs from a user of the teleoperated surgical system (e.g., a surgeon or other medical person). The control input is in communication with one or more computer-controlled teleoperated actuators, such as one or more motors to which surgical instrument 520 is coupled. In this manner, the surgical instrument 520 moves in response to a medical person's movements of the control input. In one aspect, one or more control inputs are included in a surgeon's console such as surgeon's console 16 shown at FIG. 2. A surgeon can manipulate control input devices 36 of surgeon's console 16 to operate teleoperated actuators of patient-side cart 500. The forces generated by the teleoperated actuators are transferred via drivetrain mechanisms, which transmit the forces from the teleoperated actuators to the surgical instrument 520.

Referring to FIGS. 5A-5B, in one aspect, a surgical instrument 520 and a cannula 524 are removably coupled to manipulator 512, with the surgical instrument 520 inserted through the cannula 524. One or more teleoperated actuators of the manipulator 512 move the surgical instrument 512 as a whole. The manipulator 512 further includes an instrument carriage 530. The surgical instrument 520 is detachably connected to the instrument carriage 530. In one aspect, the instrument carriage 530 houses one or more teleoperated actuators inside that provide a number of controller motions that the surgical instrument 520 translates into a variety of movements of an end effector on the surgical instrument 520. Thus the teleoperated actuators in the instrument carriage 530 move only one or more components of the surgical instrument 520 rather than the instrument as a whole. Inputs to control either the instrument as a whole or the instrument's components are such that the input provided by a surgeon or other medical person to the control input (a "master" command) is translated into a corresponding action by the surgical instrument (a "slave" response).

In accordance with some embodiments, the surgical system 10 can have multiple system actuation states including docked, following, instrument types and head-in. During a docked system state, one or more manipulator 512 have been coupled to cannula 524. During a following system state, the surgical instrument ("slave") is tracking the control input ("master" command). During an instrument-types system state, the system the system has installed in it a set of instruments suitable for performance of a particular surgical procedure or suitable for performance of a particular surgical activity during a surgical procedure. During a head-in system state, the system is waiting for the surgeon to indicate he/she has taken hold of the "master" control input device.

In an alternate embodiment, instrument carriage 530 does not house teleoperated actuators. Teleoperated actuators that enable the variety of movements of the end effector of the surgical instrument 520 are housed in a location remote from the instrument carriage 530, e.g., elsewhere on patient-side cart 500. A cable-based force transmission mechanism or the like is used to transfer the motions of each of the remotely located teleoperated actuators to a corresponding instrument-interfacing actuator output located on instrument carriage 530. In some embodiments, the surgical instrument 520 is mechanically coupled to a first actuator, which controls a first motion of the surgical instrument such as longitudinal (z-axis) rotation. The surgical instrument 520 is mechanically coupled to a second actuator, which controls second motion of the surgical instrument such as two-dimensional (x, y) motion. The surgical instrument 520 is mechanically coupled to a third actuator, which controls third motion of the surgical instrument such as opening and closing or a jaws end effector.

Figure 5C:
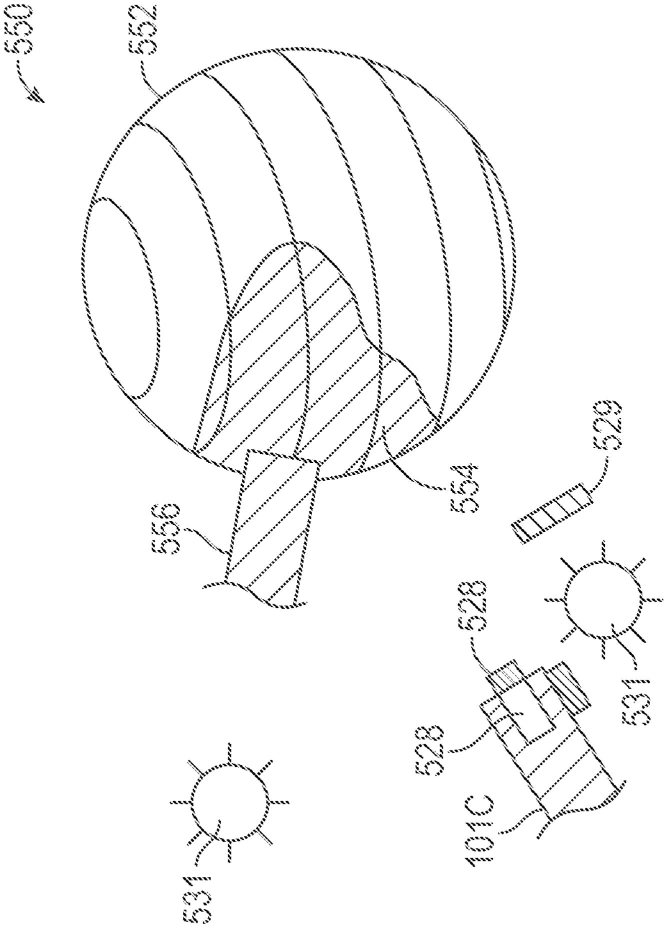
FIG. 5C is an illustrative view representing a surgical scene and also showing an endoscope mounting a camera used to record the scene and light filters to filter light wavelengths in accordance with some embodiments.

FIG. 5C is an illustrative view representing a surgical scene 550 and also showing an endoscope 101C mounting a camera 528 used to record the scene in accordance with some embodiments. The scene 550 is disposed within a patient's body cavity. The scene 550 includes an example hypothetical spherical anatomical structure 552 that includes geometric contours 554. The scene 550 encompasses a surgical instrument 556. First and second cameras 528 and 533 are mounted on an endoscope 101C to captures the scene, which is displayed within the viewer 31 and which is recorded for playback later. A selectable first light filter 528 is associated with the first camera. First and second light sources 531 are provided. A selectable second filter 529 is associated with at least one the light sources 531.

Figure 6:
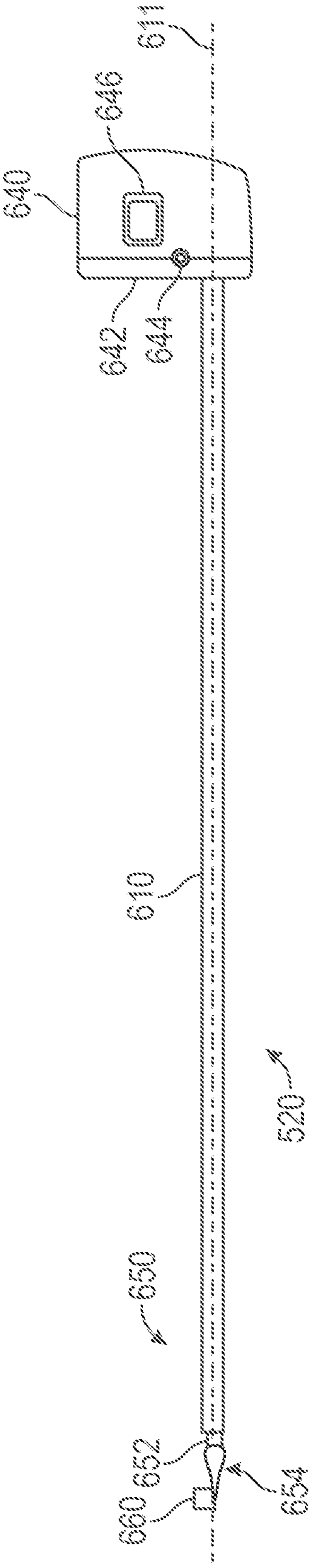
FIG. 6 is an elevation view of a surgical instrument.

FIG. 6 is a side view of a surgical instrument 520, which includes a distal portion 650 and a proximal control mechanism 640 coupled by an elongate tube 610 having an elongate tube centerline axis 611. The surgical instrument 520 is configured to be inserted into a patients body and is used to carry out surgical or diagnostic procedures. The distal portion 650 of the surgical instrument 520 can provide any of a variety of end effectors 654, such as the forceps shown, a needle driver, a cautery device, a cutting tool, an imaging device (e.g., an endoscope or ultrasound probe), or the like. The surgical end effector 654 can include a functional mechanical degree of freedom, such as jaws that open or close, or a knife that translates along a path. In the embodiment shown, the end effector 654 is coupled to the elongate tube 610 by a wrist 652 that allows the end effector to be oriented relative to the elongate tube centerline axis 611. Surgical instrument 520 can also contain stored (e.g., on a semiconductor memory associated with the instrument) information, which may be permanent or may be updatable by a surgical system configured to operate the surgical instrument 520. Accordingly, the surgical system may provide for either one-way or two-way information communication between the surgical instrument 520 and one or more components of the surgical system.

Figure 7:
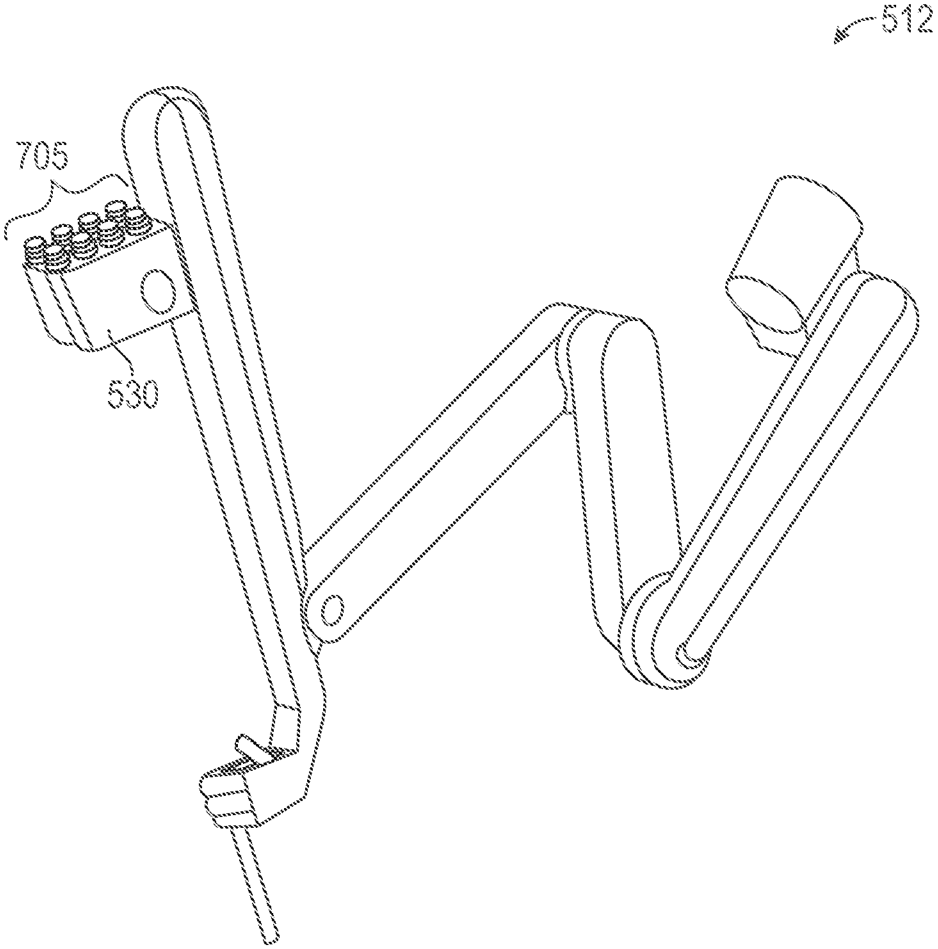
FIG. 7 is a perspective view of an instrument manipulator.

FIG. 7 is a perspective view of surgical instrument manipulator 512. Instrument manipulator 512 is shown with no surgical instrument installed. Instrument manipulator 512 includes an instrument carriage 530 to which a surgical instrument (e.g., surgical instrument 520) can be detachably connected. Instrument carriage 530 houses a plurality of teleoperated actuators. Each teleoperated actuator includes an actuator output 705. When a surgical instrument is installed onto instrument manipulator 512, one or more instrument inputs (not shown) of an instrument proximal control mechanism (e.g., proximal control mechanism 640 at FIG. 6) are mechanically coupled with corresponding actuator outputs 705. In one aspect, this mechanical coupling is direct, with actuator outputs 705 directly contacting corresponding instrument inputs. In another aspect, this mechanical coupling occurs through an intermediate interface, such as a component of a drape configured to provide a sterile barrier between the instrument manipulator 512 an associated surgical instrument.

In one aspect, movement of one or more instrument inputs by corresponding teleoperated actuators results in a movement of a surgical instrument mechanical degree of freedom. For example, in one aspect, the surgical instrument installed on instrument manipulator 512 is surgical instrument 520, shown at FIG. 6. Referring to FIG. 6, in one aspect, movement of one or more instrument inputs of proximal control mechanism 640 by corresponding teleoperated actuators rotates elongate tube 610 (and the attached wrist 652 and end effector 654) relative to the proximal control mechanism 640 about elongate tube centerline axis 611. In another aspect, movement of one or more instrument inputs by corresponding teleoperated actuators results in a movement of wrist 652, orienting the end effector 654 relative to the elongate tube centerline axis 611. In another aspect, movement of one or more instrument inputs by corresponding teleoperated actuators results in a movement of one or more moveable elements of the end effector 654 (e.g., a jaw member, a knife member, etc.) Accordingly, various mechanical degrees of freedom of a surgical instrument installed onto an instrument manipulator 512 can be moved by operation of the teleoperated actuators of instrument carriage 530.

Annotating a Recorded Video

Figure 8:
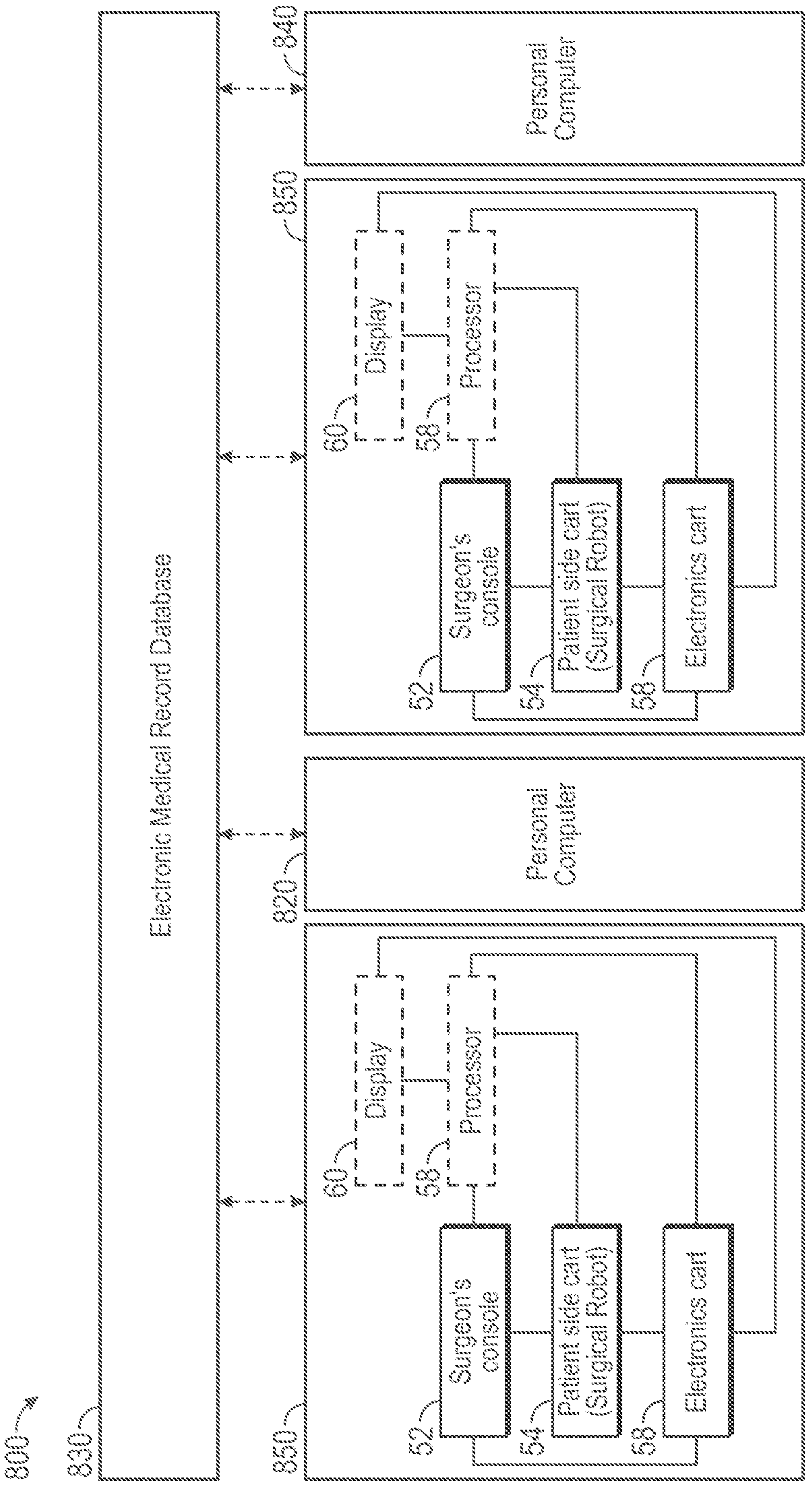
FIG. 8 is a diagrammatic illustration of a surgical planning tool.

FIG. 8 shows a schematic diagram of an exemplary surgical planning tool 800. In one aspect, surgical planning tool 800 includes a teleoperated surgical system 850 in data communication with an electronic medical device record database 830. Teleoperated surgical system 850 shown here is similar to teleoperated surgical system 850 shown at FIG. 4. In one aspect, electronic medical record database 830 includes the medical records of patients that have undergone treatment at a particular hospital or at a plurality of hospitals. Database 830 can be implemented on a server located on-site at the hospital. The medical record entries contained in the database 830 can be accessed from hospital computers through an intranet network. Alternatively, database 830 can be implemented on a remote server located off-site from the hospital, e.g., using one of a number of cloud data storage services. In this case, medical record entries of database 830 are stored on the cloud server, and can be accessed by a computer with interact access.

In one aspect, a surgical procedure is performed on a first patient using teleoperated surgical system 850. An imaging device associated with teleoperated surgical system 850 captures images of the surgical site and displays the captured images as frames of a video on a display of surgeon's console 52. In one aspect, a medical person at surgeon's console 52 highlights or annotates certain patient anatomy shown in the displayed video using an input device of surgeon's console 52. An example of such an input device is control input 36 shown at FIG. 2, which is coupled to a cursor that operates in conjunction with a graphic user interface overlaid onto the displayed video. The graphic user interface can include a QWERTY keyboard, a pointing device such as a mouse and an interactive screen display, a touch-screen display, or other means for data or text entry or voice annotation/or speech to text conversion via a microphone and processor. Accordingly, the medical person can highlight certain tissue of interest in the displayed image or enter a text annotation.

In one aspect, the surgical site video is additionally displayed on a display located on electronics cart 56. In one aspect, the display of electronics cart is a touch-screen user interface usable by a medical person to highlight and annotate certain portions of patient anatomy shown on an image that is displayed for viewing on the display on the electronics cart. A user, by touching portions of patient anatomy displayed on the touch-screen user interface, can highlight portions of the displayed image. Additionally, a graphic interface including a QWERTY keyboard can be overlaid on the displayed image. A user can use the QWERTY keyboard to enter text annotations.

In one aspect, the surgical site video captured by the imaging device associated with teleoperated surgical system 850 is recorded by the teleoperated surgical system 850, and stored on database 830, in addition to being displayed in real time or near real time to a user. Highlights and/or annotations associated with the recorded video that were made by the user can also be stored on database 830. In one aspect, the highlights made by the user are embedded with the recorded video prior to its storage on database 830. At a later time, the recorded video can be retrieved for viewing. In one aspect, a person viewing the recorded video can select whether the highlights are displayed or suppressed from view. Similarly, annotations associated with the recorded video can also be stored on database 830, in one aspect, the annotations made by the user are used to tag the recorded video, and can be used to provide as a means of identifying the subject matter contained in the recorded video. For example, one annotation may describe conditions of a certain disease state. This annotation is used to tag the recorded video. At a later time, a person desiring to view recorded procedures concerning this disease state can locate the video using a key word search.

Retrieval of Stored Video

In some cases, it is desirable for a medical person to be able to view video recordings of past surgical procedures performed on a given patient. In one aspect, a patient who previously underwent a first surgical procedure to treat a medical condition subsequently requires a second surgical procedure to treat recurrence of the same medical condition or to treat anatomy located nearby to the surgical site of the first surgical procedure. In one aspect, the surgical site events of the first surgical procedure were captured in a surgical site video recording, and the video recording was archived in database 830 as part of the patient's electronic medical records. Prior to performing the second surgical procedure on the patient, a medical person can perform a search of database 830 to locate the video recording of the patient's earlier surgical procedure.

In some cases, it is desirable for a medical person planning to perform a surgical procedure on a patient to be able to view video recordings of similar surgical procedures performed on persons having certain characteristics similar to the patient. In one aspect, surgical site video recordings of surgical procedures can be tagged with metadata information such as the patient's age, gender, body mass index, genetic information, type of procedure the patient underwent, etc., before each video recording is archived in database 830. In one aspect, the metadata information used to tag a video recording is automatically retrieved from a patient's then-existing medical records, and then used to tag the video recording before the video recording is archived in database 830. Accordingly, prior to performing a medical procedure on a patient, a medical person can search database 830 for video recordings of similar procedures performed on patients sharing certain characteristics in common with the patient. For example, if the medical person is planning to use teleoperated surgical system 850 to perform a prostatectomy on a 65 year-old male patient with an elevated body mass index, the medical person can search database 830 for surgical site video recordings of prostatectomies performed using teleoperated surgical system 850 on other males of similar age and having similarly elevated body mass index.

In one aspect, a video recording of a surgical procedure is communicated by database 830 to an optional personal computer 820 (as indicated by dashed line), and made available for viewing by a medical person who plans to perform a surgical procedure. Additionally or in the alternative, the video recording of the earlier surgical procedure can be communicated by database 830 to teleoperated surgical system 850, and made available for viewing preoperatively or intraoperatively. In one aspect, the video recording is displayed by teleoperated surgical system 850 on a display located on surgeon's console 52. In another aspect, the video recording of the first surgical procedure is displayed on a display located on electronics cart 56.

Cloud-Based Video Database

In one aspect, database 830 is implemented on a remote server using a cloud data storage service and is accessible by multiple health care providers. Referring to FIG. 8, as shown by dashed line, surgical planning tool 800 optionally includes teleoperated surgical system 850 (as indicated by dashed line) and personal computer 840 (as indicated by dashed line). In one aspect, teleoperated surgical system. 850 is similar to teleoperated surgical system 850 and personal computer 840 is similar to personal computer 820, except that teleoperated surgical system 850 and personal computer 820 are located at a first health care provider and teleoperated surgical system 850 and personal computer 840 are located at a second location or even with a second health care provider. In one aspect, a first patient requires surgical treatment of a medical condition, and undergoes a surgical procedure using teleoperated surgical system 850 at the first health care provider. A video recording of the surgical procedure is archived on database 830. At a later time, a second patient requires surgical treatment of the same medical condition, and plans to receive surgical treatment using teleoperated surgical system 850 at the second health care provider, Prior to performing the surgical procedure on the second patient, a medical person accesses database 830 through a secure internet connection and searches database 830 for surgical site video recordings of similar procedures. In one aspect, the medical person treating the second patient is able to retrieve from database 830 the video recording of the first patient's surgical procedure, without acquiring knowledge of the identity of the first patient. In this manner, the privacy of the first patient is maintained. In one aspect, the video recording of the first patient's surgical procedure includes highlights and/or annotations made by the medical person who treated the first patient.

Computer Based Pattern Matching and Analysis

Surgical planning tool 800 can includes a pattern matching and analysis algorithm implemented in the form of computer executable code. In one aspect, the pattern matching and analysis algorithm is stored in a non-volatile memory device of surgical planning tool 800, and is configured to analyze the video recordings archived in database 830. As discussed previously, each of the video recordings archived in database 830 can be tagged and/or embedded with certain metadata information. This metadata information can include patient information such as patient age, gender, and other information describing the patient's health or medical history. Additionally, as discussed previously, the metadata information can include highlights or annotations made by a medical person. In one aspect, these highlights and annotations are embedded with the video recording and archived together with the video in database 830.

In one aspect, pattern matching and analysis algorithms include an image analysis component that identifies patterns in shapes and colors that are shared amongst multiple video recordings stored on database 830. The pattern matching and analysis algorithm then reviews the tagged metadata associated with this subset of video recordings to determine whether any words or phrases are frequently associated with videos within this subset. These analyses performed by pattern matching and analysis algorithms can be used to assist medical persons in making determinations about patient anatomy, preferred surgical approaches, disease states, potential complications, etc.

Surgical Information Atlas

Figure 9:
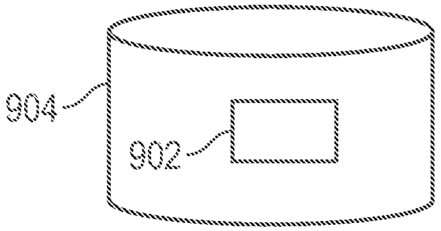
FIG. 9 is an illustrative drawing representing a surgical information atlas stored within a non-transitory storage device in accordance with some embodiments.

FIG. 9 is an illustrative drawing representing a surgical information atlas 902 stored within a non-transitory storage device 904 within the medical records database 830 in accordance with some embodiments. The surgical instrument atlas stores information produced in association with surgical procedures. For example, images displayed during a surgical procedure can be recorded for storage in the information atlas 902. Some video images may be clear i.e., not enhanced, some images may include Near Band Imaging (NBI) information, some image may contain optical coherence tomography (OCT) information, some images may include Raman spectroscopy information, some images may include fluorescence information, some images may include hyperspectral imaging information, and some may include CT information, for example. Moreover, information such as surgical instrument kinematic information and surgical stage information such as surgical system actuation state and surgical instrument actuations state, also are recorded at different points in a surgical procedure. Surgical system actuation states include one or more of kinematic positions of system arms, cart location, and information related to master control positions for example. Different surgical instruments have different actuation states. Surgical instrument actuation states include instrument kinematics which include but are not limited to pitch, yaw, roll and jaw location, for example. During a surgery or after a surgery, a user such as a surgeon or another member of a surgical team, may annotate recorded video image information of a surgical scene such as NBI images, Raman spectroscopy images, OCT images, fluorescence images or hyperspectral images with metadata that indicate anatomical structures of particular interest such as blood vessels, tumors, dysplasia, nervous, or connective tissues for example. The annotations may include one or more of or a combination of written notes tagged to recorded motion picture information and/or coloring or highlighting (e.g., telestration) of images in the video recordings, for example. The recorded information is used to build a surgical information atlas 902 that provides associations between surgical image information, surgical stage information, information associated with an instance of a surgical procedure is stored in a surgical record information structure.

Figure 10:
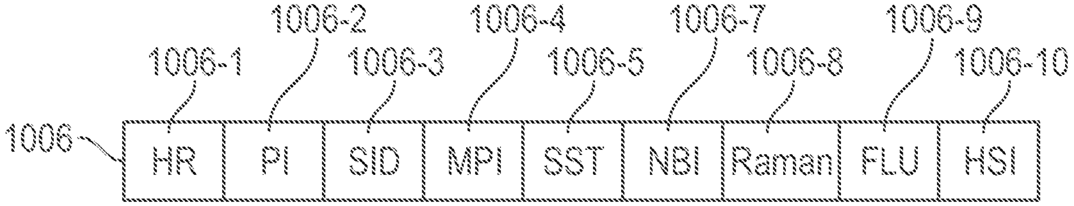
FIG. 10 is an illustrative drawing showing certain details of an example surgical record information structure stored within the surgical information atlas in accordance with some embodiments.

FIG. 10 is an illustrative drawing showing certain details of an example surgical record information structure 1006 stored within the surgical information atlas 902 in accordance with some embodiments. A patient health record field (HR) 1006-1 provides information about the patient who is operated upon such as age, body mass, blood type, height, sex, and race, for example. A physician information field (PI) 1006-2 provides information about the surgeon who performs the individual operation such as level of experience in general and level of experience operating a robot-assisted surgical system, for example. A surgical system identifier field (SID) 1006-3 provides information about the surgical system used to perform the operation such as make, model and serial number, for example. A motion picture images field (MPI) 1006-4 provides information such as motion picture images recorded during a surgery. A surgical stage field (SST) 1006-5 provides surgical system actuation state information and surgical instrument actuation state information recorded during a surgery. An NBI field (NBI) 1006-6 provides information such as motion picture images recorded using NBI during a surgery. A Raman field (Ram) 1006-7 provides information such as motion picture images recorded using Raman spectroscopy during a surgery. A fluorescence field (Flu) 1006-8 provides information such as motion picture images recorded using fluorescence during a surgery. An HSI field (HIS) 1006-9 provides information such as motion picture images recorded using hyperspectral imaging during a surgery. A surgical annotation field (Ann) 1006-10 provides annotation information such as descriptive information or expert analysis associated with the surgical procedure represented in the information structure.

Display Modalities

As used herein, a "clear" image of a surgical scene is an image that is presented without special enhancement, Many display modalities exist to enhance the display of surgical images including: Near Band Imaging (NBI), Raman spectroscopy, fluorescence, hyperspectral imaging (HSI) and computer tomography, for example. Each of these enhancement techniques has advantages.

Figure 11:
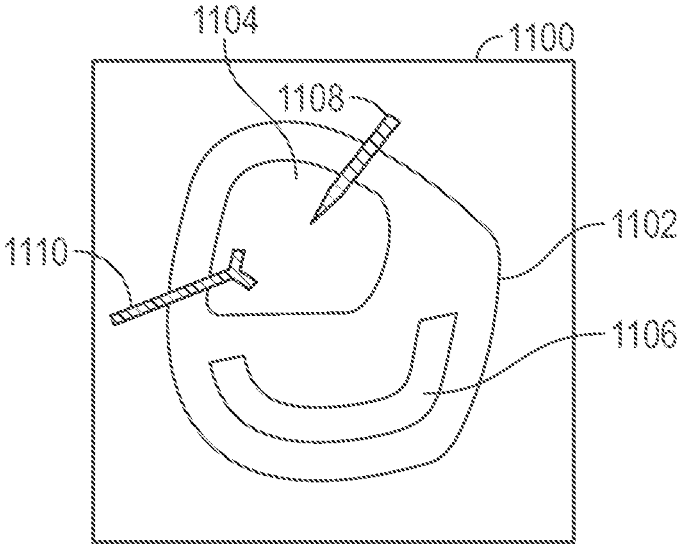
FIG. 11 an illustrative drawing representing an example clear image of a surgical scene in accordance with some embodiments.

FIG. 11 an illustrative drawing representing an example clear image of a surgical scene 1100 captured by a camera 528 of an endoscope display device 101C for display within a viewer 31 in accordance with some embodiments. More particularly, light produced by a light source 531 is reflected from a surgical scene 551 and is captured by camera 528, which produces image first information that can be used to configure the computer 58 to generate a clear display image of the surgical scene 551. A tissue region 1102 includes a first anatomical object 1104 and a second anatomical object 1106. In the example surgical scene 1100, the first anatomical object 1104 can include a prostate or a uterus for example. The second anatomical object 1106 can include a nerve, a ureter, or the cervix, for example. A first surgical instrument 1108 and a second surgical instrument 1100 are shown disposed within the surgical scene 1100. The first surgical instrument 1108 can include a forceps or a needle driver, for example. The second surgical instrument 1110 can include a scissor or other instrument equipped to deliver monopolar, bipolar or ablative energy for example.

Figure 12:
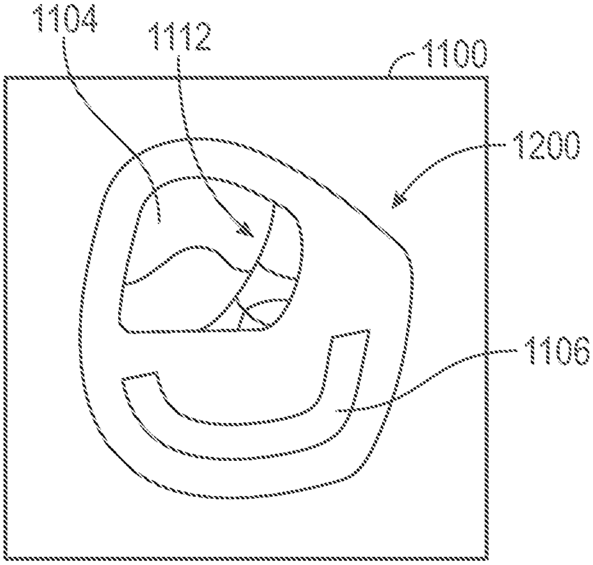
FIG. 12 is an illustrative drawing representing an example Narrow Band Image (NBI) modality image of the example surgical scene of FIG. 11 in which images of anatomical structures within a first anatomical object are enhanced through an NBI display modality.

FIG. 12 is an illustrative drawing representing the example NBI modality image 1200 of the surgical scene 1100 of FIG. 11 in which an image of vascular anatomical structures 1112 within a first anatomical object 1104 are enhanced through a Narrow Band Imaging display modality. Narrow Band Imaging (NBI) is an optical imaging technique that improves the visibility of blood vessels 1112 and other structures beneath a tissue surface. NBI modality images are produced through shining filtered light upon a surgical scene. More particularly, ambient light 531 is filtered using filter 529 to provide specific blue and green wavelengths at which peak light absorption of hemoglobin occurs. Reflected light is captured by a camera 528, which produces corresponding second image information, which includes NBI modality image information. The filtered light is shined on anatomical tissue in order to enhance the details of blood vessels, which will appear very dark, allowing for their improved visibility and in the improved identification of other surface structures. The shorter wavelengths only penetrates a top layer of tissue structure, while the longer wavelengths penetrate deeper into it. The shorter wavelength is absorbed by capillary vessels near the surface and is particularly useful for detecting tumors, which are often highly vascularized. The longer wavelength is absorbed by blood vessels located deeper within the tissue, which appears as a different from the shallower vessels that absorbed the shorter wavelength light. The more deeply penetrating longer wavelength light allows a better understanding of the vasculature of suspect lesions located more distant from the tissue surface. Thus, NBI can enhance the visibility of blood vessel structures within an anatomical object within in a surgical scene.

Figure 13:
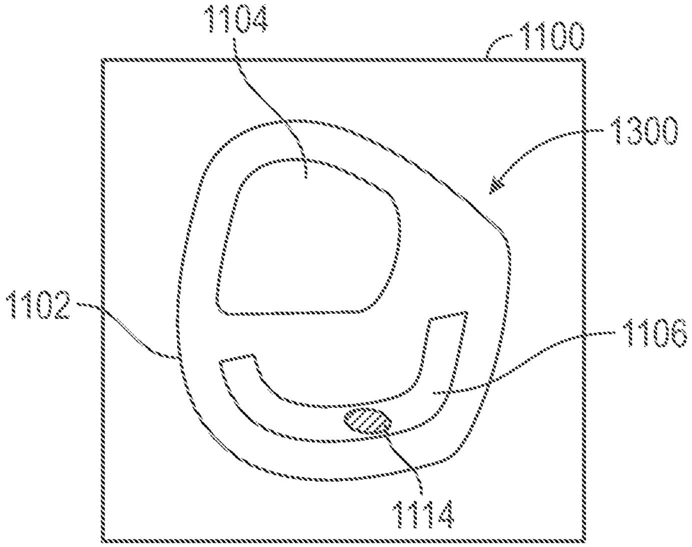
FIG. 13 is an illustrative drawing representing an example Raman spectroscopy modality image of the example surgical scene of FIG. 11 in which images of anatomical structures within a second anatomical object are enhanced through a Raman spectroscopy display modality.

FIG. 13 is an illustrative drawing representing the example Raman spectroscopy modality image surgical scene 1100 of FIG. 11 captured with a camera 528 in which an image of a tumor anatomical structure 1114 within a second anatomical object 1106 is enhanced through a Raman spectroscopy display modality. Light reflected from a surgical scene is captured by camera 528. The computer 58 is configured for use to perform Raman spectroscopy optical imaging processing of the captured images to produce the third (Raman spectroscopy) image information. Raman spectroscopy involves measuring the chemical composition of complex biological samples based upon the reflected light and to produce Raman spectroscopy image information. Certain tumor tissues 1114, for example, have a higher water content than normal anatomical tissue, and therefore, are distinguishable from surrounding tissue based upon their water content. A Raman spectrum provides quantitative information regarding a tissue's chemical makeup. Specifically, Raman spectroscopy is a technique that can be used to observe inelastic scattering of light by vibrating molecules and can provide chemical fingerprints of cells, tissues or biofluids. Raman spectroscopy relies on scattering of light by molecules and information regarding the vibrational modes of the molecules can be obtained using visible or near-infrared lasers. A common method for obtaining Raman spectral images is to raster-scan a sample through a laser spot or to scan the laser spot across the sample, and to then apply a uni- or multivariate spectral model to each Raman spectrum. Thus, Raman spectroscopy can enhance the visibility of anatomical structures within an anatomical object based upon constituent chemical makeup.

Fluorescence is a display modality used to detect fluorescently labelled structures during a surgical procedure. For example, fluorescence can be used to highlight a visual image of labeled or unlabeled tissue structures that fluoresce vs those that do not fluoresce. Fluorescence guided surgery (FGS) can be performed using imaging devices that provide real time simultaneous information from color reflectance images and fluorescence emission. Fluorescence modality images are produced through filtering light reflected from a surgical scene. More particularly, one or more light sources 531 are used to excite and illuminate an anatomical tissue region. Camera 528 receives light reflected from the surgical scene that is filtered with an optical filter 529 that matches the emission spectrum of a fluorophore and produces fourth image information, which includes enhanced fluorescence image information.

Figure 14:
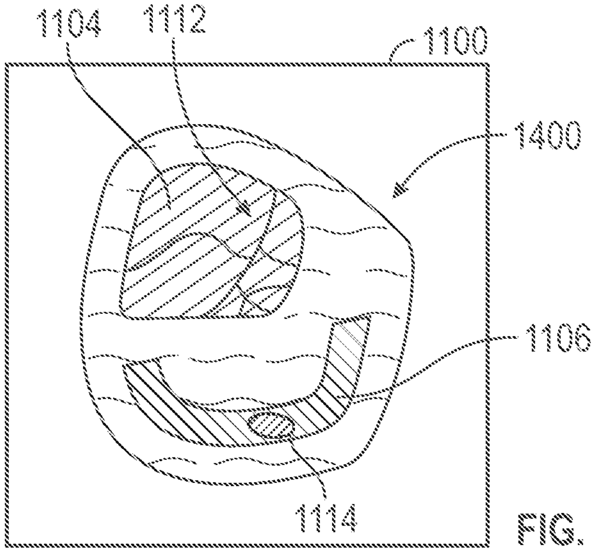
FIG. 14 is an illustrative drawing representing an example hyperspectral (IBS) modality image of example surgical scene of FIG. 11 displayed using a HIS imaging display modality.

FIG. 14 is an illustrative drawing representing the example hyperspectral image 1400 of the surgical scene 1100 of FIG. 11 displayed using a hyperspectral imaging display modality. Hyperspectral imaging (HSI) combines digital imaging and spectroscopy techniques. A hyperspectral camera 533 captures light reflected from the surgical scene that includes, for each pixel in an image, light intensity (radiance) for a large number (typically a few tens to several hundred) of contiguous spectral bands. Every pixel in the image thus contains a continuous spectrum (in radiance or reflectance) and can be used to characterize the objects in the scene with great precision and detail, More particularly, for each pixel of an image. HSI, acquires a three-dimensional dataset called a hypercube, with two spatial dimensions and one spectral dimension. The computer 58 is configured for use to perform processing that spatially resolves spectral imaging obtained by HSI to provide enhanced visual information about the tissue physiology, morphology, and composition to produce fifth (HSI) image information. HSI can provide a far more detailed visual image of a surgical scene than a normal color camera, which typically only acquires three different spectral channels corresponding to the visual primary colors red, green and blue. HSI also provides the ability to identify objects or disease conditions based on the chemical composition of tissue within the field of view of the sensor. Thus, hyperspectral imaging leads to a vastly improved ability to visually differentiate between the objects in the scene based on their spectral properties.

Figure 15:
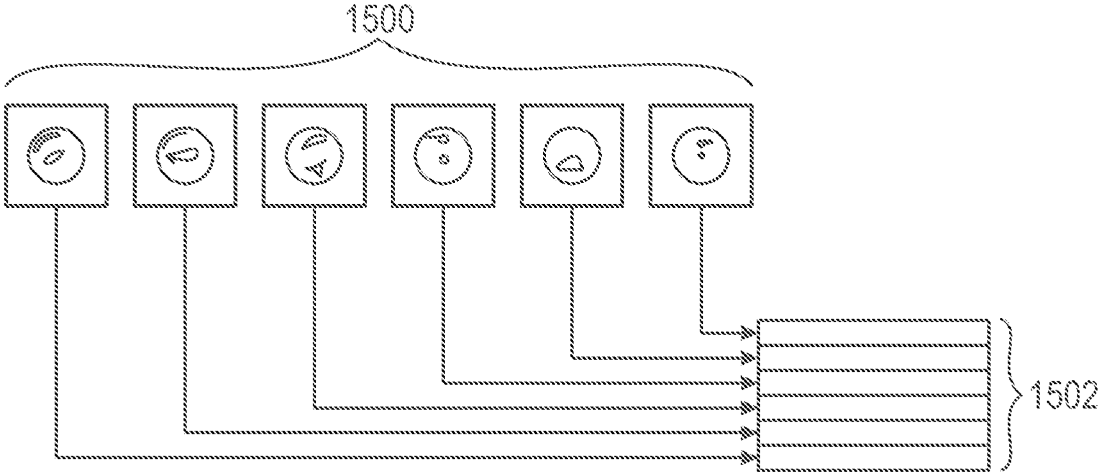
FIG. 15 is an illustrative drawing representing a computer tomographic slice display modality of the example surgical scene of FIG. 11 in accordance with some embodiments.

FIG. 15 is an illustrative drawing representing computer tomographic slice display modality of the example surgical scene 1100 of FIG. 11 in accordance with some embodiments. The computer tomographic (CT) slices combines images 1500 produced using a radiation source, typically X-ray radiation, taken from different angles to produce virtual two dimensional (planar) cross-sectional image slices 1502 of specific anatomical objects allowing a surgeon to see inside the object without cutting. Cross-sectional images 1502 at different three-dimensional depths within an anatomical object can be separately displayed to provide a visual representation of the internal structures within the object.

Multi-Modality Display Formats

Certain display modalities may be better suited than others for imaging certain kinds of anatomical structures. For example, anatomical structures such as surface vasculature or dysplasia often can be displayed more visibly using NBI. However, disease states such as cancer margins often can be more visibly displayed using Raman spectroscopy, for example. Moreover, anatomical structures that can be labeled with fluorescence markers, or respond to excitation light with different emissions on their own ('endogenously') often can be more visibly displayed using fluorescence, for example. Furthermore, anatomical structures that have unique spectral properties often can be more visibly displayed using hyperspectral imaging, for example.

Moreover, certain display modalities may be better suited than others for use during certain stages of a surgical procedure. More particularly, for example, an NBI display often is used during an initial planning stage for a head and neck surgical procedure. Raman spectroscopy often is used during the post-excision procedure stage, but can be used in vivo when combined with raman-active particles. Fluorescence often is used before and after the tissue excision surgical procedure stage. Hyperspectral imaging often is used during the planning portion of a surgical procedure.

In accordance with some embodiments, a multitude of different display formats are provided from which to select to display a surgical scene that simultaneously uses multiple display modalities. A stitch format stitches together video images from two or more different display modalities of a single scene so that a single surgical scene is produced having different portions represented using different display modalities. In a stitch format, different image modalities are used to represent different portions of an overall image of a surgical scene such that only one image modality is visible at any given point within a stitched region of an overall image. A picture-in-picture (PiP) format displays a first primary, typically full-screen, video image of the surgical scene using a first display modality and displays a reduced size insert video (or still) image of the surgical scene using a second display modality within a portion of the display. An overlay format overlays an image using one display modality onto an image using a different display modality. In an overlay format, different image modalities can be used to represent a single portion of an overall image of a surgical scene such that an overlaying image is partially transparent to permit an overlaid portion to be visible beneath it.

Stitch Format

Figure 16:
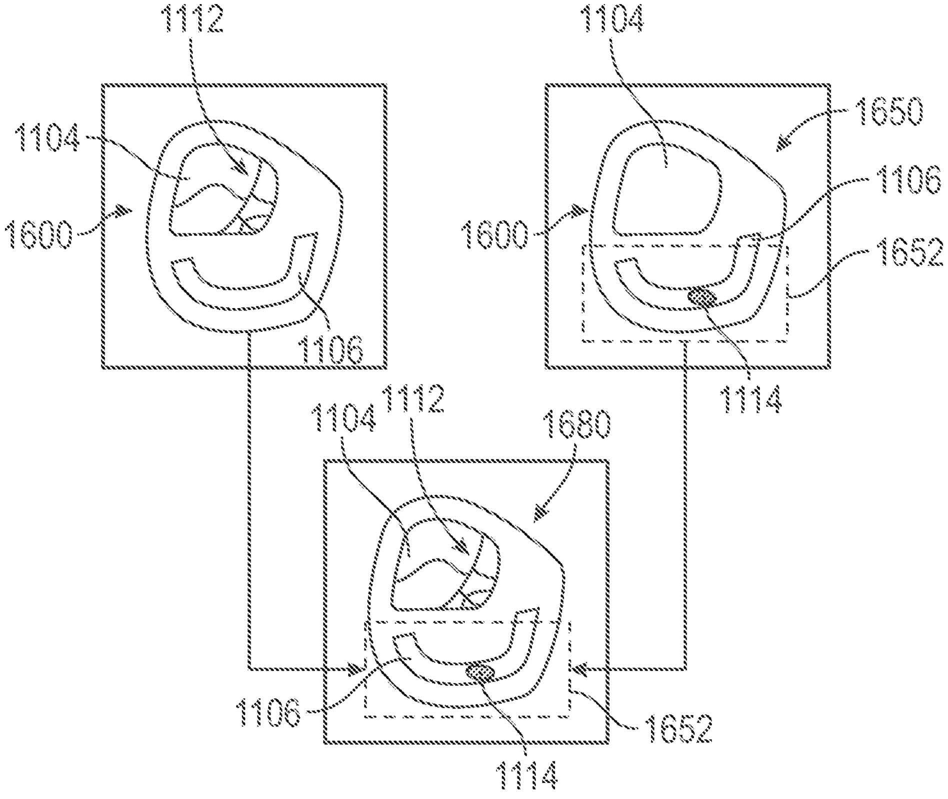
FIG. 16 is an illustrative example multi-modality display of the surgical scene of FIG. 11 using multiple display modalities combined using a stitch format in accordance with some embodiments.

FIG. 16 is an illustrative example multi-modality display of the surgical scene 1100 of FIG. 11 using multiple display modalities combined using a stitch format in accordance with some embodiments. A first surgical image 1600 of the surgical scene is produced using the NBI modality. A second image 1650 of the surgical scene 1100 is produced using the Raman spectroscopy modality. It is noted that in the first image 1600, certain blood vessel structures 1112 are readily visible but a tumor structure 1114 within the second anatomical object 1106 is not as clearly visible. Conversely, in the second image 1650, the tumor structure 1114 is readily visible, but the blood vessel structures 1112 are not as readily visible. A third image 1680 is produced in which a selected portion 1652 of the second display 1650 image and the first display image 1600 are stitched together. It will be appreciated that both images produced using the NBI modality and Raman spectroscopy modality can be produced during a surgical procedure. In accordance with some embodiments, display rules can determine what portions of one image modality to stitch into a different image modality. In the example in FIG. 16, a tumor-containing portion 1652 of the Raman spectroscopy display modality of the second display image 1650 is stitched into the first display image. Thus, in the example of FIG. 16, an image of a critical anatomical structure that is more readily visible in the Raman spectroscopy modality is stitched into an NBI modality which is better suited to display of vascular structures, for example.

Figure 17:
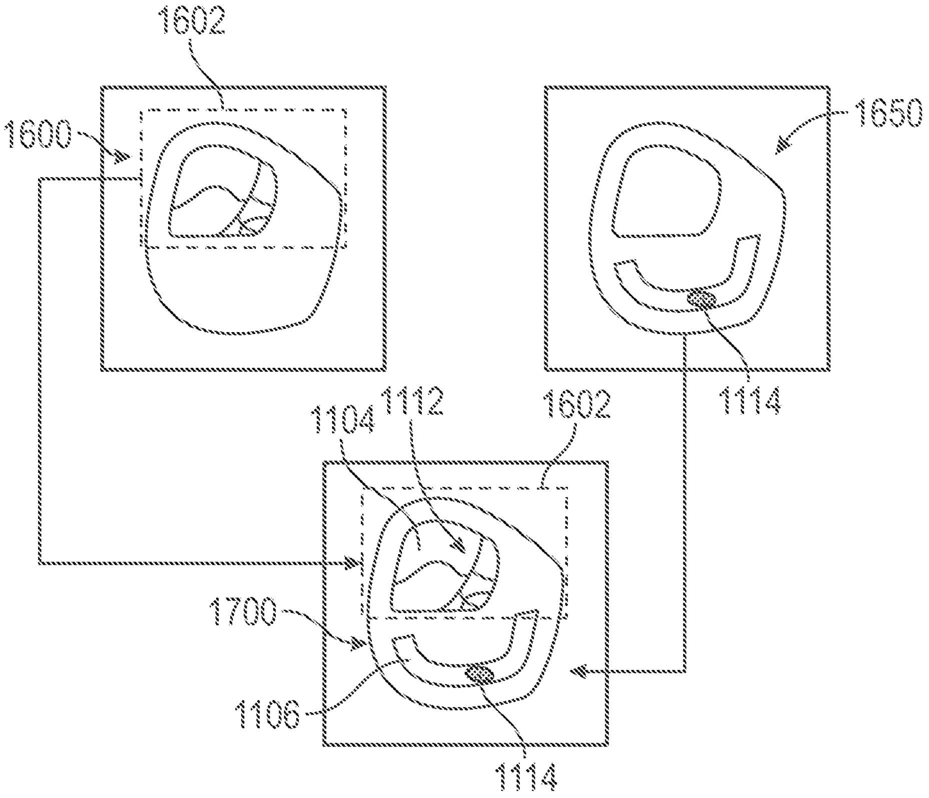
FIG. 17 is an illustrative alternative example multi-modality display of the surgical scene of FIG. 11 using multiple display modalities combined using a stitch format in accordance with some embodiments.

FIG. 17 is an illustrative alternative example multi-modality display of the surgical scene 1100 of FIG. 11 using multiple display modalities combined using a stitch format in accordance with some embodiments. A first image 1600 of the surgical scene is produced using the NBI modality. A second image 1650 of the surgical scene 1100 is produced using the Raman spectroscopy modality. In FIG. 17, a fourth display image 1700 of the surgical scene 1100 is produced in which a selected portion 1602 of the first display 1600 image and the second display image 1650 are stitched together. A portion 1602 of the NBI display modality of the first display image 1600 that contains significant vascular imagery 1112 is stitched into the second display image. Thus, images of a critical anatomical structure that is more readily visible in the NBI modality is stitched into Raman spectroscopy modality which is better suited to display of tumor structures, for example.

Picture-in-Picture Format

Figure 18:
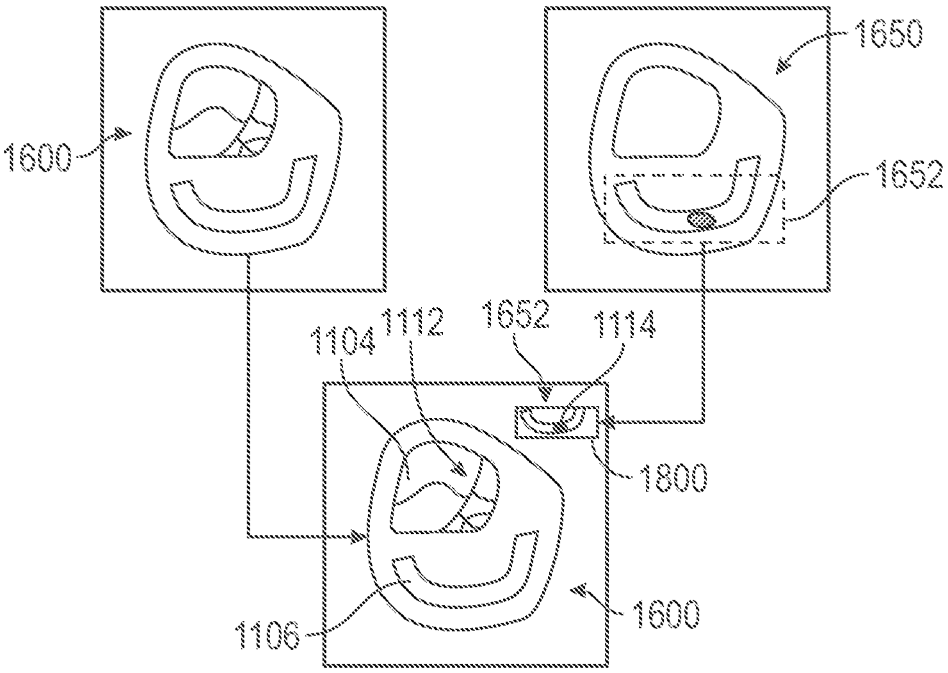
FIG. 18 is an illustrative example multi-modality display of the surgical scene of FIG. 11 using multiple display modalities combined using a picture-in-picture format in accordance with some embodiments.

FIG. 18 is an illustrative example multi-modality display of the surgical scene 1100 of FIG. 11 using multiple display modalities combined using a picture-in-picture (PiP) format in accordance with some embodiments. The surgical images of FIG. 18 correspond to those of FIG. 16. However, in FIG. 18, the portion 1652 of the second image 1650 produced using the Raman spectroscopy modality is included as a reduced size PiP image 1800 within a primary first image 1600 produced using the NBI modality.

Figure 19:
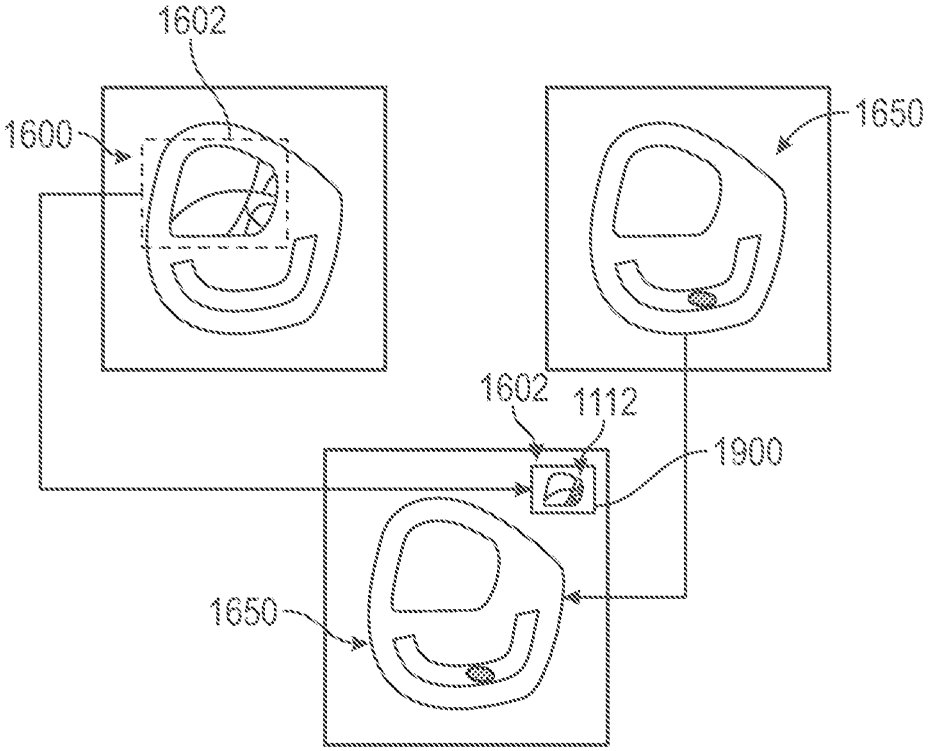
FIG. 19 is an illustrative alternative example multi-modality display of the surgical scene of FIG. 11 using multiple display modalities combined using a picture-in-picture format in accordance with some embodiments.

FIG. 19 is an illustrative alternative example multi-modality display of the surgical scene 1100 of FIG. 11 using multiple display modalities combined using a picture-in-picture (PiP) format in accordance with some embodiments. The surgical images of FIG. 19 correspond to those of FIG. 17. However, in FIG. 19, the portion 1602 of the first image 1600 produced using NBI modality spectroscopy modality is included as a reduced size PiP image 1900 within a primary second image 1650 produced using the Raman spectroscopy modality.

Annotation Format

Figure 20:
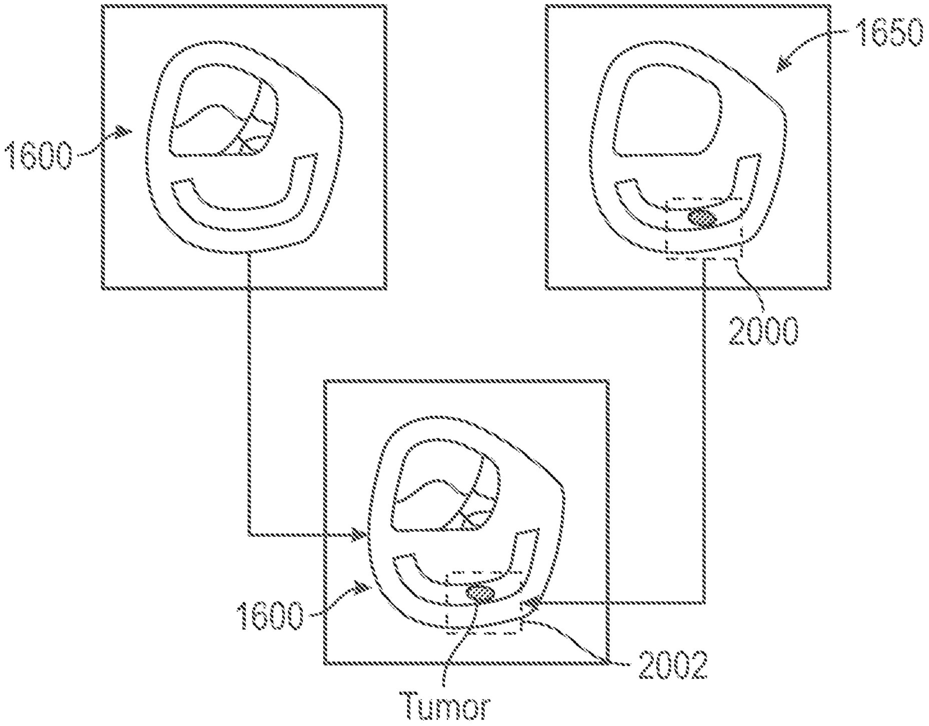
FIG. 20 is an illustrative example display of the surgical scene of FIG. 11 using information from multiple display modalities using an annotation format in accordance with some embodiments.

FIG. 20 is an illustrative example display of the surgical scene 1100 of FIG. 11 using information from multiple display modalities using an annotation format in accordance with some embodiments. The surgical images of FIG. 20 correspond to those of FIGS. 16-17. However, in FIG. 20, information determined from a portion 2000 of the second image 1650 produced using the Raman spectroscopy modality is included as an annotation 2002 within a primary first image 1600 produced using the NBI modality. The example annotation provides an overlay tumor image 2002 determined from the second image 1650 and corresponding explanatory text, e.g. "tumor".

Dynamic Presentation of Multi-Modality Displays

Figure 21A:
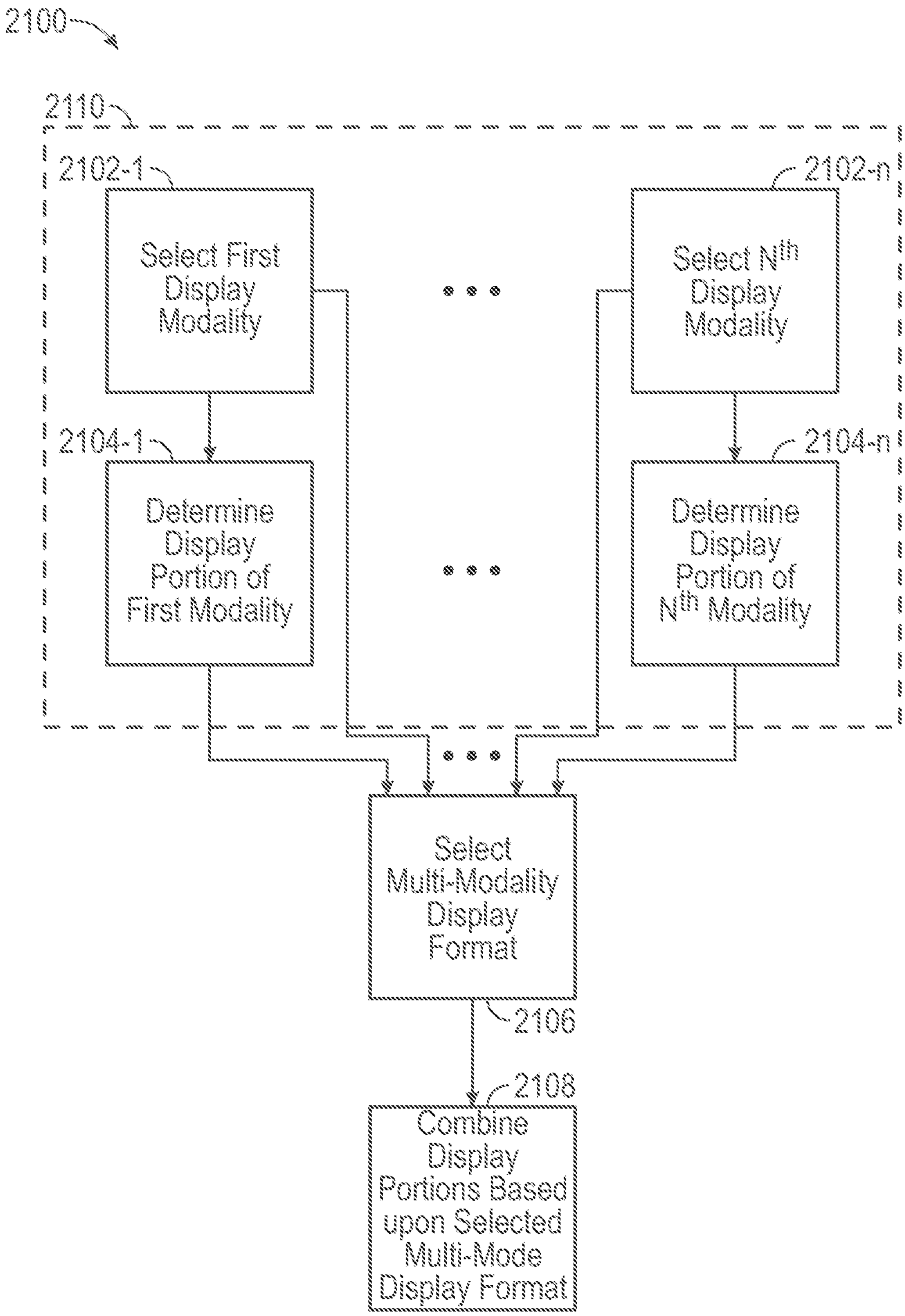
FIG. 21A is an illustrative flow diagram representing a first process to dynamically present a multi-modality surgical image in accordance with some embodiments.
Figure 21B:
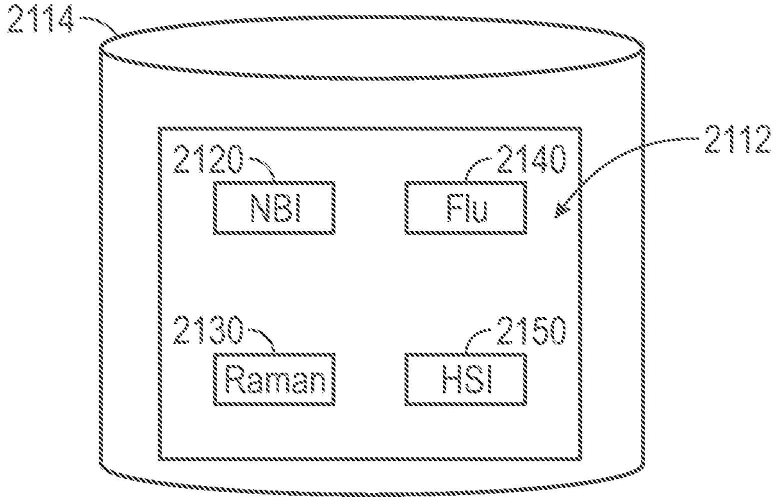
FIG. 21B is an illustrative drawing representing respective first image information stored in a non-transitory storage device that can be used to produce different image modality images.
Figure 21C:
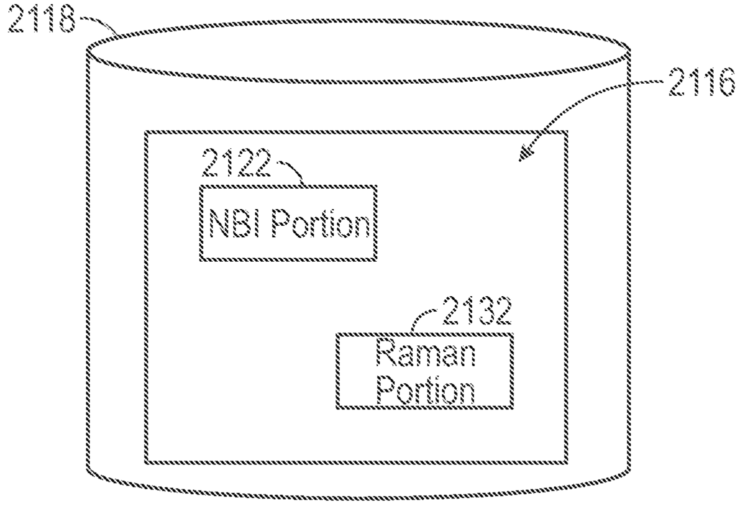
FIG. 21C is an illustrative drawing representing respective second image portion information stored in a non-transitory storage device that can be used to produce different image modality image portions.

FIG. 21A is an illustrative flow diagram representing a first process 2100 to dynamically present a multi-modality surgical image in accordance with some embodiments. FIG. 21B is an illustrative drawing representing respective first image information 2112 captured using a camera 528 and stored in a non-transitory storage device 2114 that can be used to produce different image modality images. FIG. 21C is an illustrative drawing representing respective second image portion information 2116 captured using a camera 528 and stored in a non-transitory storage device 2118 that can be used to produce different image modality image portions. The first process 2100 is described with reference to the surgical system 10.

Modality selection blocks 21024 to 2102-*n* configure a computer processor 58 to select and produce one or more of a first through an nth display modality. Information used to produce the images can be stored for use to produce composite multi-modality images that display multiple image modalities. An illustrative embodiment described herein includes NBI, Raman spectroscopy, fluorescence, HSI, OCT, and CT display modalities. It will be appreciated that different image data can be required to produce the different display modalities. More specifically, different image data may require use of different portions of the light spectrum. For example, NBI modality images generally require certain blue and green wavelengths. Raman spectroscopy images generally require different wavelengths depending on the tissue of interest. Fluorescence images generally require visible and near-infrared wavelengths. HSI generally requires wavelengths throughout the visible and infrared regions. Therefore, data for different image modalities sometimes may be separately captured and processed in the course of a surgical procedure. For example, a surgeon may choose to first observe a fluorescent image and to later observe an NBI image and after that to observe a composite multi-modality image that includes portions from both the fluorescent and NBI images.

The storage device 2116 in FIG. 21B stores example NBI image information 2120 that can be used to configure the computer 58 to generate a full-screen NBI modality image such as image 1200 of FIG. 12 within the viewer 31. The device 2116 stores Raman spectroscopy information 2130 that can be used to configure the computer 58 generate a fill-screen Raman modality image such as image 1300 of FIG. 13 within the viewer 31. The device 2116 stores fluorescence information 2140 that can be used to configure the computer 58 to generate a full-screen fluorescence modality image (not shown). The device 2116 stores HSI information 2150 that can be used to configure a computer 58 to generate a full-screen HSI modality image such as image 1400 of FIG. 14 within the viewer 31.

Portion selection blocks 2104-1 to 2104-*n* configure the computer 58 to select and select respective portions of one or more of the selected display modalities. Different portions of different image modalities may be selected for display in a composite multi-modality image. For example a portion of an NBI modality image that shows blood vessels may be selected. A different portion of a Raman spectroscopy modality image that shows a tumor may be selected. The storage device 2118 in FIG. 21C stores example NBI image portion information 2122 that can be used to configure the computer 58 to generate an NBI modality image portion such as image portion 1602 shown in FIG. 17. The storage device 2118 in FIG. 21C stores example Raman spectroscopy image portion information 2132 that can be used to configure the computer 58 to generate a Raman spectroscopy modality image portion such as image portion 1652 shown in FIG. 16. It will be appreciated that in some embodiments, the image portion information 2122 is stored embedded within image portion information 2120, and image portion information 2132 is stored embedded within image information 2130.

Format selection block 2106 configures the computer 58 to select a multi-modality display format based upon selected display modalities and corresponding selected display portions. Block 2108 configures the computer 58 to simultaneously display multiple image modalities of a single surgical scene, according to a multi-modality display format selected using format selection block 2106.

For example, in some embodiments, a modality selection block 2102-1 configures the computer 58 to select and produce an NBI image modality. Portion selection block 2104-1 configures the computer 58 to determine certain anatomical structures within the NBI image, such as blood vessels for example.

In addition, for example, in some embodiments, a modality selection block **2102-*n* configures the computer 58 to select a Raman spectroscopy image modality. Portion selection block 2104-*n* configures the computer 58** to determine certain anatomical structures within a Raman image, such as a tumor for example.

Other modality selection blocks (not shown) and other portion selection blocks (not shown) select other display modalities, e.g., fluorescence or HSI, and corresponding anatomical structures and portions of each.

The format selection block 2106 determines whether a modality is to be displayed as primary (e.g., full-screen) or as an insert portion, and determines modalities to be stitched together, modalities to be displayed as a PiP, and determines modality information to be indicated using an annotation. The display generation block 2108 configures the computer 58 to cause display of the formatted multi-modality image on a computer display screen.

Figure 22:
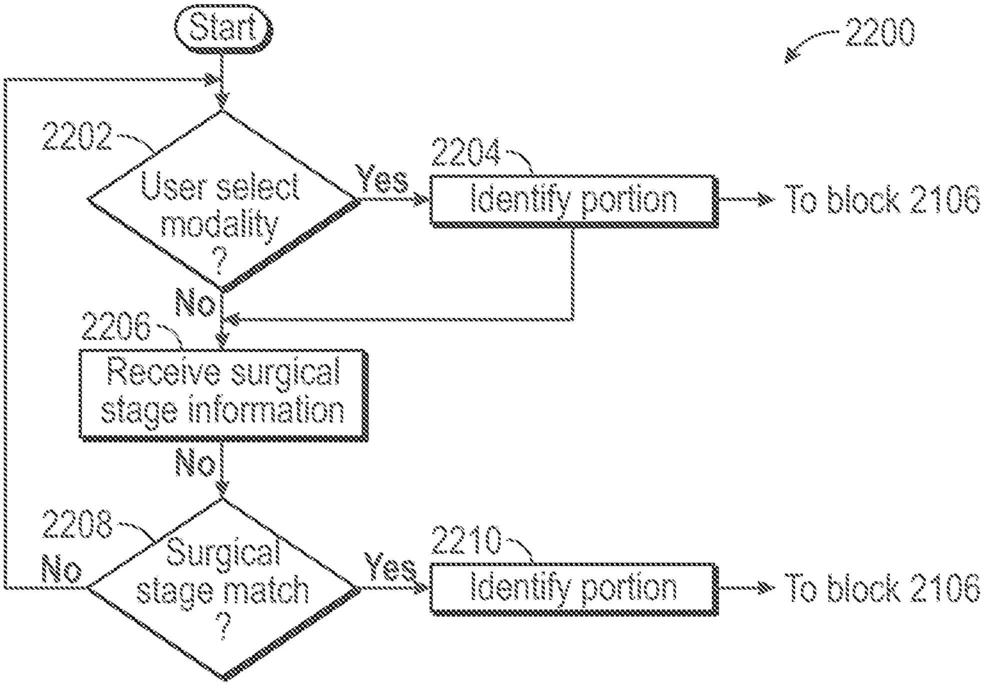
FIG. 22 is an illustrative flow diagram representing details of a sub-process to select display modalities and portions of selected display modalities in accordance with some embodiments.

FIG. 22 is an illustrative flow diagram representing details of a sub-process 2200 to select display modalities and portions of selected display modalities in accordance with some embodiments. The sub-process 2200 is described with reference to the surgical system 10. In some embodiments, the sub-process 2200 implements the modality selection blocks 2102-1 to **2102-*n* and portion selection blocks 2104-1 to 2104-*n* shown within of dashed lines 2110 in FIG. 11. Decision block 2202 configures the computer 58 to determine whether a user has selected a display modality. In response to a determination that a user has selected a display modality, block 2204 configures the computer 58 to select a portion of the user-selected display modality that contains an image of an anatomical structure of interest. Following a selection using block 2204 or in response to decision block 2202 determining that a user has not selected a display modality, control flows to block 2206, which configures the computer 58 to receive surgical stage information from the surgical system 10. In some embodiments, the surgical stage information includes surgical system actuation state information and surgical instrument kinematic information, for example. Decision block 2208 configures the computer system 58 to determine whether the received surgical stage information matches an image selection rule corresponding to an image modality. In response to a determination that the received surgical stage information matches an image selection rule, block 2210 configures the computer 58 to select a portion of the matching display modality that contains an image of anatomical structure of interest. In response to a determination by block 2208 that there is no surgical stage match, control flows back to decision block 2202**.

It will be appreciated from FIG. 22 that different user selections and different surgical stage matches may occur at different points during performance of a surgical procedure using the surgical system 10. Thus, the process 2200 can select and generate different image modalities and different portions at different times during a surgical procedure.

Figure 23:
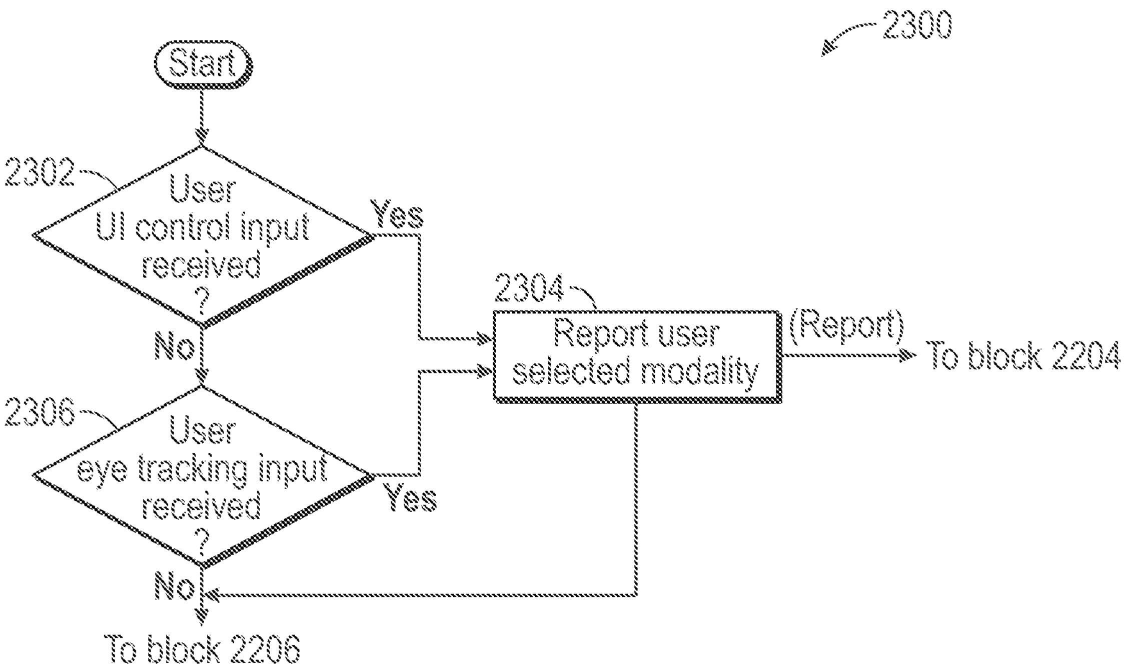
FIG. 23 is an illustrative flow diagram representing details of a sub-process to receive user selection of an image modality in accordance with some embodiments.

FIG. 23 is an illustrative flow diagram representing details of a sub-process 2300 to receive user selection of an image modality in accordance with some embodiments. The sub-process 2300 is described with reference to the surgical system 10. In some embodiments, the sub-process 2300 implements the decision making block 2202 of FIG. 22. Decision block 2302 configures the computer 58 to determine whether user input is provided to user control inputs 36 to select an image display modality. In response to a determination that user input is provided to control inputs 36 to select an image modality, block 2304 configures the computer 58 to report the user selected modality to block 2204. In response to decision block 2302 determining that no user input is provided to user control inputs 36, decision block 2306 configures the computer 58 to determine whether user eye tracking input is provided selects an image modality. In response to a determination that user eye tracking input is provided to select an image modality, block 2304 configures the computer 58 to report the user selected modality to block 2204. Following reporting block 2304 or following decision block 2306, whichever is the case, control flow returns to block 2206.

It will be appreciated from FIG. 23 that different user selections may occur at different points during the performance of a surgical procedure using the surgical system 10. It will be further appreciated that the sub-process 2300 continues to cycle during a surgical procedure, to continually check for changes in user input. Thus, the process 2300 can select from among different image modalities at different times during a surgical procedure.

FIG. 24 is an illustrative drawing representing an example modality selection user interface UI 2402 displayed within a viewer 31 of the surgical system AA in accordance with some embodiments. The illustrative modality selection UT display provides a selection of modalities in a left column and receives user input to a right column to indicate a user's modality selection. In some embodiments, a user makes a selection using control inputs 36. In the example modality selection UI, the user has selected the NBI and fluorescence modalities. The decision block 2302 of FIG. 23 configures the computer to determine what duly modality selections a user makes using the modality selection UI display of FIG. 24.

Figure 25C:
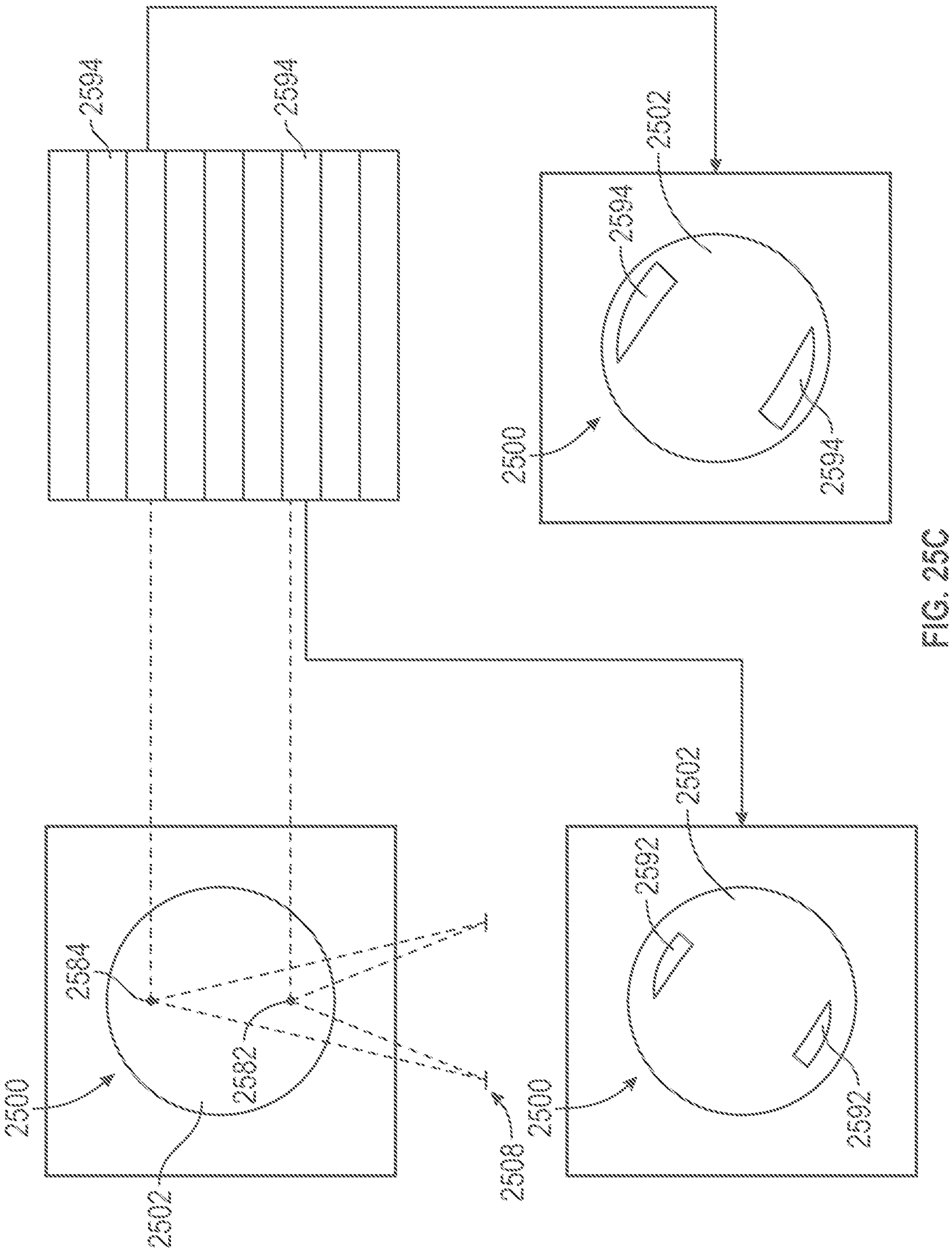

FIGS. 25A-C are illustrative drawings presenting two dimensional eye tracking (FIGS. 25A-25B) and in-depth eye tracking (FIG. 25C) in accordance with some embodiments. Eye sensors 47 disposed adjacent where a user looks into the viewer 31 track user eye movement. Referring to FIG. 25A a full-screen display has a first modality image 2500, such as a clear modality and displays an anatomical structure 2502, and has a first stitched-in portion 2504 having a second modality such as HSI, centered near a first region 2506 where a user's eyes 2508 gaze. Referring to FIG. 25B, the full-screen display having the first modality image 2500 that displays the anatomical structure 2502 has a second stitched-in portion 2552 having the second modality centered near a second region 2556 where a user's eyes 2508 gaze. In accordance with some embodiments, a user gaze lasting at least two seconds is required to trigger the option for generation of a stitched-in portion in a region near the user's gaze.

It will be appreciated that an HSI modality image can be desirable because of the image sharpness and the detailed information included in the image. However, an HSI image typically requires significant processing power to produce. Producing an HSI modality image for only that portion of a display that a user gazes at reduces processing requirements, which can enhance overall image processing efficiency. In some embodiments, the control input can be actuated to select a planar eye tracking mode of operation. The decision block 2306 configures the computer to determine what if any planar eye tracking selections a user makes.

Referring to FIG. 25C, a screen display showing the anatomical structure 2502 next to a stack of CT depth slices of the anatomical structure shown in the display. A user's eye gaze is shown focused at a first depth 2582. The user's eye gaze also is shown focused at a second depth 2584. A first CT slice 2592 corresponding to the first depth 2582 is overlaid onto the screen display 2500 showing the anatomical structure 2502 in response to the user's eye gaze at the first depth 2582. A second CT slice 2594 corresponding to the second depth 2584 is overlaid onto the screen display 2500 showing the anatomical structure 2502 in response to the user's second eye gaze. In accordance with some embodiments, a user gaze lasting at least two seconds is required to trigger generation of an overlaid CT slice at a depth of the user's gaze. In some embodiments, the control input can be actuated to select a depth eye tracking mode of operation. The decision block 2306 configures the computer to determine what if any depth eye tracking selections a user makes.

Figures 26, 27:
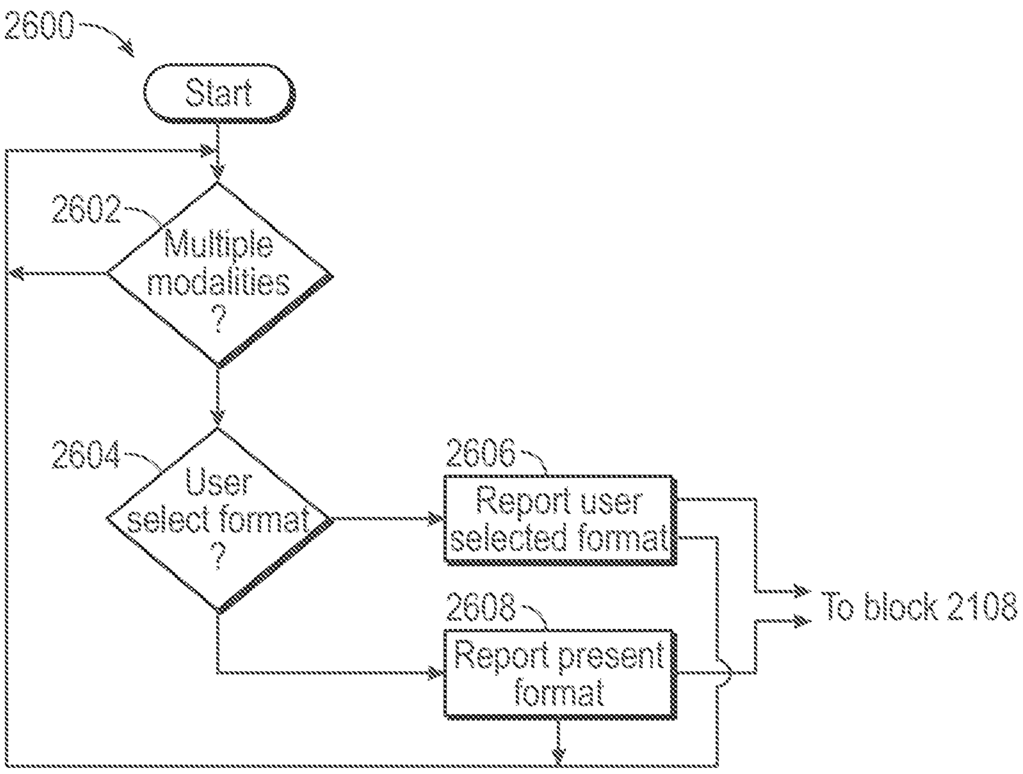
FIG. 26 is an illustrative flow diagram representing details of a sub-process to select a multi-modality display format in accordance with some embodiments.
FIG. 27 is an illustrative drawing representing an example format selection user interface UI displayed within a viewer of the surgical system in accordance with some embodiments.

FIG. 26 is an illustrative flow diagram representing details of a sub-process 2600 to select a multi-modality display format in accordance with some embodiments. The sub-process 2300 is described with reference to the surgical system 10. In some embodiments, the sub-process 2300 implements the format selection block 2106 of FIG. 11. Decision block 2602 configures the computer 58 to determine whether multiple modalities are selected. In response to a determination that multiple modalities are not selected, control flows back to decision block 2602. In response to a determination that multiple modalities are selected, decision block 2604 determines whether a user designates a user-selected format. In response to a determination that a user designates a user-selected format, block 2606 reports the user-selected format to block 2108, and control next flows back to decision module 2602. In response to a determination that a user has not designated a user-selected format priority, block 2608 reports a preset format priority to block 2108, and control next flows back to decision block 202.

It will be appreciated from FIG. 26 that a user can designate different formats and format priorities at different points during performance of a surgical procedure using the surgical system 10. It will be further appreciated that the sub-process 2600 continues to cycle during a surgical procedure, to continually check for changes in user format selections. Thus, the process 2600 can select from among different modality formats at different times during a surgical procedure.

FIG. 27 is an illustrative drawing representing an example format selection user interface UI 2702 displayed within a viewer 31 of the surgical system AA in accordance with some embodiments. The illustrative format selection UI 2702 provides a presentation priority section 2704 that lists modalities in a left column and receives user input to a middle and right columns to indicate a user's presentation priority selection. In the example presentation priority section 2706, the user has selected both clear and NBI for the primary presentation, which is full-screen in some embodiments, and has selected Raman, Fluorescence and HSI for insert presentation (stitch, PiP or annotate). The x1 and x2 designations of NBI and clear, respectively, indicate an example prioritization as between NBI and clear in which NBI has a higher priority. For example, according to the example prioritization, if the NBI modality is present, then the NBI modality will be primary, but if NBI is absent, then the clear modality will be primary. The illustrative format selection UI 2702 also provides a presentation style section 2706 that lists presentation styles (stitch, PiP or annotate) in a left column and receives user input to a right column to indicate a user's presentation style selection. In the example presentation style section 2706, the user has selected PiP. Thus, in the example user format selection, NBI is presented as primary and one or more of Raman. Fluorescence and HSI is presented in PiP within the NBI screen. The decision block 2608 of FIG. 26 configures the computer to determine what if any format priority selections a user makes using the format selection UI display of FIG. 27.

Figures 28, 29:
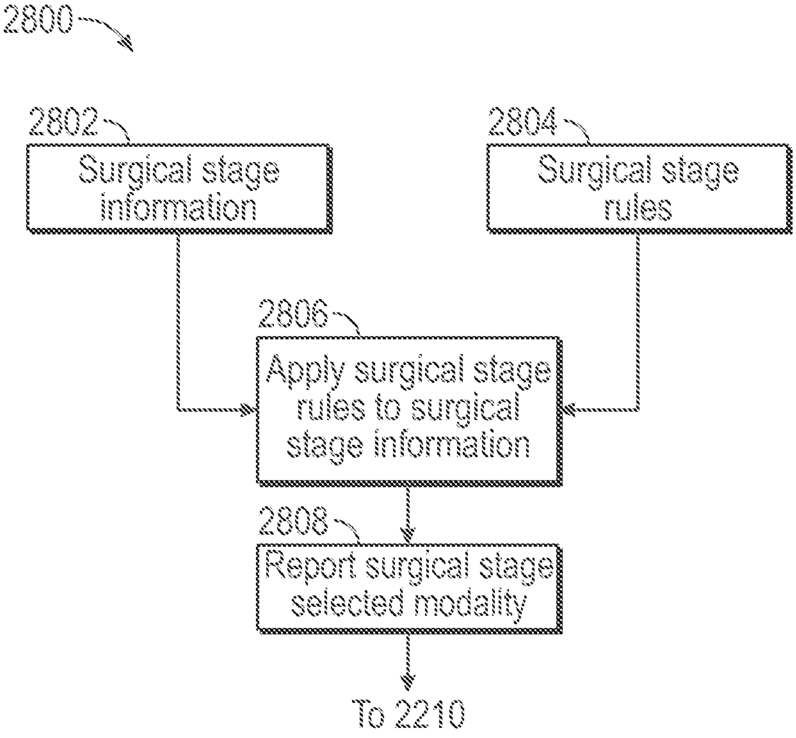
FIG. 28 is an illustrative flow diagram representing certain details of a sub-process to determine whether surgical stage information and corresponding surgical stage rules together indicate a display modality in accordance with some embodiments.
FIG. 29 is an illustrative drawing representing example surgical stage signatures and corresponding modalities in accordance with some embodiments.

FIG. 28 is an illustrative flow diagram representing details of a sub-process 2800 to determine whether surgical stage information and corresponding surgical stage rules together indicate a display modality in accordance with some embodiments. The sub-process 2800 is described with reference to the surgical system 10. In some embodiments, the sub-process 2800 implements the decision block 2208 of FIG. 22. Block 2802 configures the computer 58 to receive surgical stage information such as system actuation state and surgical instrument kinematics. In some embodiments, the surgical stage information can include additional information such as patient health record information and surgeon information such as experience level, for example. Block 2804 configures the computer to receive surgical stage rules for the surgical procedure. Block 2806 configures the computer to apply the received surgical stage rules to the received surgical stage information to determine whether the rules indicate that the received surgical stage information matches a display modality. Block 2808 configures the computer to report the display modality, if one corresponds.

FIG. 29 is an illustrative drawing representing example information structure 2902 including surgical stage signatures stored in a storage device within the computer system 58 and corresponding modalities in accordance with some embodiments. Respective surgical stage signatures correspond to respective display modalities. In accordance with some embodiments, an occurrence during a surgery using a surgical system, of surgical stage information that closely matches a surgical stage signature can indicate that the surgical system should use a display modality that corresponds to the matching surgical stage vector. In accordance with some embodiments, machine learning techniques can be used to generate surgical stage signatures based upon information stored within the surgical information atlas 902. More specifically, for example, classifiers can be used together with expert knowledge to correlate surgical stage signatures with image modalities. Each surgical stage signature (SigSS) includes a multi-dimensional vector. The vector includes vector values that are indicative of attributes of a surgical stage that correspond to an image modality. In some embodiments, surgical system signatures are produced based upon recorded system state information and recorded surgical instrument kinematic motion information recorded for a multiplicity of surgical procedures using a multiplicity of different surgical systems. In some embodiments, for example, surgical instrument kinematic motion is decomposed into a multiple vector component representing kinematic features such as instantaneous velocity, instantaneous acceleration, instantaneous three-dimensional positon, current path of motion and predicted path of motion, for example. Moreover, in some embodiments, not only is motion and position of an instrument important to determination of surgical stage signatures, but also context information such as physical location of an anatomical structure relative to the instrument, physical location of other instruments, a patient's health and the nature of a surgery be relevant to interpretation of an kinematic information. Moreover, previous instrument motions can be relevant to determination of a surgical stage signature, such as where to what imam modality corresponds to a particular surgical stage signature. Thus, in some embodiments, surgical stage signatures also can include vectors indicative of location of anatomical structures, location of other instruments, patient health, type of surgery, physician experience level and prior motion of an instrument, for example.

Referring again to FIG. 28, block 2806 performs a correlation between surgical stage signatures, which act as rules, and received surgical stage information to determine whether there is a close enough match between the received surgical stage information and a surgical stage signature to trigger a report to use a display modality that corresponds to the received surgical stage information. It will be appreciated that in machine learning embodiments a match is determined based upon a range of similarity between the received instrument kinematics and system state information, etc. and rules represented by the surgical state signatures. Thus, in some embodiments for example, a surgical stage information that is within some threshold distance from a certain rule is determined to match that rule, which triggers selection of a corresponding display modality.

Figures 30, 31:
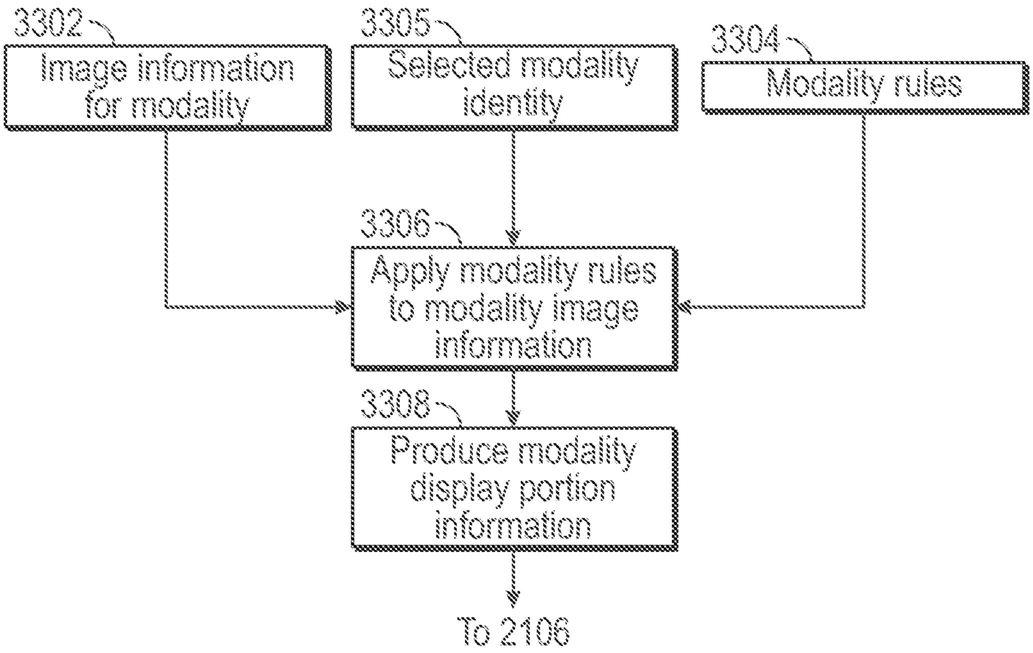
FIG. 30 is an illustrative flow diagram representing certain details of a sub-process to generate an image modality portion in accordance with some embodiments.
FIG. 31 is an illustrative drawing representing example image signatures and corresponding annotations in accordance with some embodiments.

FIG. 30 is an illustrative flow diagram representing details of a sub-process 3000 to generate an image modality portion in accordance with some embodiments. The sub-process 3000 is described with reference to the surgical system 10. In some embodiments, the sub-process 3000 implements blocks 2204 and 2210 of FIG. 22. Block 3002 configures the computer to receive image information captured using a camera 528 for a selected image modality for a surgery being performed using a surgical system. The received image information can include anatomic structure location, margin assessment and functional information, for example. In some embodiments, the image information can be accompanied by additional information such as patient health record information and surgeon information such as experience level, for example. Block 3004 configures the computer to receive image modality rules. Block 3005 configures the computer system to receive information that identifies an image modality that corresponds to the received image information and to the received rules. Block 3006 configures the computer to apply the received image modality rules to the received image information to identify a portion of the image modality that is likely to be of greatest interest to a surgeon, and therefore, should be selected for insertion into another image when appropriate to feature the important portion. Block 3008 configures the computer to report the portion, if one is identified that corresponds.

It will be appreciated that the sub-process 3000 is performed separately for each image modality currently in use by a surgical system 10 performing a surgical procedure. More particularly, for example, if only the NBI and Raman spectroscopic image modalities are currently in use, then the sub-process 3000 is performed separately for NBI image information and NBI rules and for Raman image information and Raman rules. Moreover, it will be appreciated that different portions of an overall scene may be identified for the different image modalities. For example, the NBI modality can be superior at identifying blood vessels and the Raman modality can be superior at identifying tumors.

FIG. 31 is an illustrative drawing representing example information structure 3102 that includes image signatures stored in a storage device within the computer system 58 and corresponding annotations in accordance with some embodiments. Respective image signatures correspond to respective anatomical structures, such as blood vessels or tumors, for example, which are likely to be of special interest to a surgeon during a surgery. An annotation can provide an explanation of potential relevance of a surgical image produced during a surgery that closely matches an image signature associated with the annotation. A portion of image modality information that matches an image signature is selected to insert (e.g., via stitch, PiP or annotation) into an overall surgical scene displayed within the viewer 31.

In accordance with some embodiments, machine learning techniques can be used to generate image signatures based upon information stored within the surgical information atlas 902. More specifically, for example, classifiers can be used together with expert knowledge to correlate image signatures with image modalities. Each image signature (SigIM) includes a multi-dimensional vector. A vector includes values that are indicative of an anatomical structure. In some embodiments, image signatures are produced based upon factors such as analyses of anatomical structure shape, spectral signature, depth and color information captured in an image modality. It will be appreciated that different image modalities can be suited to capture images of different anatomical structures.

Referring again to FIG. 30, block 3006 performs a correlation between image signatures, which act as rules, and received image information to determine whether there is a close enough match between the received image information and an image signature to trigger a report to use a portion of an image that corresponds to the received image information. It will be appreciated that in machine learning embodiments a match is determined based upon a range of similarity between the received image information and rules represented by the image signatures. Thus, in some embodiments for example, image information that is within some threshold distance from a certain rule is determined to match that rule, which triggers selection of a corresponding portion of the image for display within another image.

Although illustrative embodiments have been shown and described, a wide range of modification, change and substitution is contemplated in the foregoing disclosure and in some instances, some features of the embodiments may be employed without a corresponding use of other features. One of ordinary skill in the art would recognize many variations, alternatives, and modifications. Thus, the scope of the disclosure should be limited only by the following claims, and it is appropriate that the claims be construed broadly and in a manner consistent with the scope of the embodiments disclosed herein.

What is claimed is:

1. A method to produce a multi-modality image, on a display of a surgical scene at a surgical site, comprising:

using at least one camera to capture light reflected from the surgical scene;

producing first image information, in a non-transitory storage device, that includes a first modality image of the surgical scene that provides a first type of enhancement to image data for improved visibility of a first anatomical structure based upon light captured using the at least one camera;

producing second image information, in the non-transitory storage device, that includes a second modality image of the surgical scene that provides a second type of enhancement to the image data for improved visibility of a second anatomical structure based at least upon light captured using the at least one camera;

matching image information of a second portion of the second modality image with image signature information, wherein the image signature information is stored in the non-transitory storage device and comprises a multi-dimensional vector comprising values indicative of the second anatomical structure generated from images of the second anatomical structure of previous surgeries;

selecting the second portion of the second modality image based at least upon anatomical structured information included within the selected portion matching the image signature information, stored in the non-transitory storage device; and configuring a computer to display simultaneously within the display of the surgical scene, for the first anatomical structure at least a first portion of only the first modality image of the surgical scene within a region of the surgical scene using the first image information and for the second anatomical structure the selected second portion of only the second modality image of the surgical scene within a different region of the surgical scene using the second image information.

2. The method of claim 1, further including:

comparing the second image information with image signature information stored in the non-transitory storage device to select the second portion of the second modality image.

3. The method of claim 1, further including:

comparing the second image information with a plurality of image signatures stored in a non-transitory storage device to select the second portion of the second modality image.

4. The method of claim 1, wherein configuring includes configuring to the computer to stitch the second portion of the second modality image into the first modality image in place of a corresponding first portion of the first modality image.

5. The method of claim 1, wherein configuring includes configuring to the computer to include simultaneously within the display, the at least the first portion of the first modality image and a reduced size image of the second portion of the second image modality.

6. The method of claim 1, wherein the second image information includes anatomical structure location information; further comprising:

selecting the different region of the display in which to display the second portion of only the second modality image, based at least in part upon the anatomical structure location information included within the second image information.

7. The method of claim 1 further comprising:

tracking user eye focus location within the display; and configuring the computer to select the different region in which to display the second portion of only the second modality image, based at least in part upon tracked user eye focus within the different region of the display.

8. The method of claim 1, further comprising:

configuring the computer to include simultaneously within the display, the at least the first portion of only the first modality image and a reduced size image of the second portion of only the of the second modality image.

9. The method of claim 1, further comprising:

tracking surgical stage in the course of a surgical procedure;

wherein configuring the computer includes configuring the computer to display simultaneously within the display at least the first portion of only the first modality image of the surgical scene within the region of the display and the at least the second portion of only the second modality image of the surgical scene within the different region of the display, based at least in part upon the tracked surgical stage.

10. The method of claim 1, tracking surgical stage in the course of a surgical procedure wherein tracking surgical stage includes at least one of surgical system actuation state information or surgical instrument kinematic information, indicating stage of surgery; and wherein configuring the computer includes configuring the computer to display simultaneously within the display at least the first portion of only the first modality image of the surgical scene within the region of the display and the at least the second portion of only the second modality image of the surgical scene within a different region of the display, based at least in part upon the tracked surgical stage.

11. The method of claim 9 further including:

comparing the surgical stage information with a plurality of surgical stage signatures stored in the non-transitory storage device storage device to select the modality image format.

12. The method of claim 1 further including:

using a first filter configured to pass reflected only light within a first wavelength range to the at least one camera; and using a second filter configured to pass reflected only light within a second wavelength range to the at least one camera.

13. The method of claim 1, wherein the first modality includes one of clear, Near Band Imaging, Raman spectroscopy, fluorescence, hyperspectral imaging; and wherein the second modality includes a different one of Near Band Imaging, Raman spectroscopy, fluorescence, hyperspectral imaging.

14. A system to produce a multi-modality image, on a display screen of a surgical scene at a surgical site, comprising:

a processor;

a memory device holding an instruction set executable on the processor to cause the surgical system to perform operations comprising:

using at least one camera to capture light reflected from the surgical scene;

producing first image information, in a non-transitory storage device, that includes a first modality image of the surgical scene that provides a first type of enhancement to image data for improved visibility of a first anatomical structure based upon light captured using the at least one camera;

producing second image information, in the non-transitory storage device, that includes a second modality image of the surgical scene provides a second type of enhancement to image for improved visibility of a second anatomical structure data based at least upon light captured using the at least one camera;

matching image information of a second portion of the second modality image with image signature information, wherein the image signature information is stored in the non-transitory storage device and comprises a multi-dimensional vector comprising values indicative of the second anatomical structure generated from images of the second anatomical structure of previous surgeries;

selecting the second portion of the second modality image based at least upon anatomical structured information included within the selected portion matching the image signature information; and configuring a computer to display simultaneously within the display, for the first anatomical structure at least a first portion of only the first modality image of the surgical scene within a region of the display using the first image information and for the second anatomical structure the selected second portion of only the second modality image of the surgical scene within a different region of the display using the second image information.

15. The system of claim 14, the operations further comprising:

tracking user eye focus location within the display;

selecting the different region in which to display the portion of only the second modality image, based at least in part upon tracked user eye focus within the different region of the display.

16. The system of claim 14, the operations further comprising:

tracking surgical stage in the course of a surgical procedure;

wherein configuring the computer includes configuring the computer to display simultaneously within the display, at least the portion of only the first modality image of the surgical scene within the region of the display and the at least the portion of only the second modality image of the surgical scene within a different region of the display based at least in part upon the tracked surgical stage, based at least in part upon the tracked surgical stage.

17. The system of claim 14, wherein the second image information includes anatomical structure location information; further operations including:

selecting the different region of the display in which to display the portion of only the second modality image within, based at least in part upon the anatomical structure location information included within the second image information.

18. The system of claim 14 further including:

a first filter configured to pass reflected only light within a first wavelength range to the at least one camera; and a second filter configured to pass reflected only light within a second wavelength range to the at least one camera.

19. The system of claim 14, wherein the first modality includes one of clear, Near Band Imaging, Raman spectroscopy, fluorescence, hyperspectral imaging; and wherein the second modality includes a different one of Near Band Imaging, Raman spectroscopy, fluorescence, hyperspectral imaging.

20. The system of claim 14, the operations further including:

configuring the computer to stitch the portion of the second modality image into the first modality image in place of a corresponding portion of the first modality image.

* * * * *